United States Patent [19]

Jantzen et al.

[11] Patent Number: 5,846,278
[45] Date of Patent: Dec. 8, 1998

[54] METHOD OF DETERMINING GLASS DURABILITY

[75] Inventors: Carol Maryanne Jantzen; John Butler Pickett, both of Aiken, S.C.; Kevin George Brown, Augusta, Ga.; Thomas Barry Edwards, Aiken, S.C.

[73] Assignee: Westinghouse Savannah River Company, Aiken, S.C.

[21] Appl. No.: 684,553

[22] Filed: Jul. 19, 1996

[51] Int. Cl.$^6$ .................................................... C03B 1/00
[52] U.S. Cl. .................. 65/17.1; 65/29.12; 65/29.16; 588/12; 588/252; 588/901
[58] Field of Search .................. 65/17.1, 29.12, 65/29.16, 30.12, 61, 111, 135.9; 588/12, 252, 901

[56] References Cited

U.S. PATENT DOCUMENTS

| 5,102,439 | 4/1992 | Jantzen | 65/29 |
| 5,401,693 | 3/1995 | Bauer et al. | 501/38 |

FOREIGN PATENT DOCUMENTS

| 0 588 251 A1 | 3/1994 | European Pat. Off. | C03C 13/00 |

OTHER PUBLICATIONS

M. Pourbaix, *Atlas of Electrochemical Equilibria in Aqueous Solutions*, English translation of 1966, French version by J.A. Franklin (Ed), National Association of Corrosion Engineers, Houston, Texas (1974) pp. 1–644 (no month avail).

D. G. Brookins *Eh–pH Diagrams for Geochemistry*, Springer–Verlag, New York (1988) (no month avail).

Jantzen, "Characterization of Defense Waste Processing Facility (DWPF) Startup Frit,"U.S. DOE Report WSR-C–RP–89–18, Westinghouse Savannah River Co., Savannah River Laboratory, Aiken, S.C. (1989) (no month avail).

Schumacher, "Errors of DWPF Frit Analysis—Final Report," U.S. DOE Report WSRC–RP–92–37, Westinghouse Savannah River Co., Savannah River Technology Center, Aiken, S.C. (Jan., 1992).

Boyd, et al., Kirk–Othmer *Encyclopedia of Chemical Technology, Fourth Edition* "Glass," (Editor: Mary Howe–Grant; Publishers: John Wiley & Sons, New York, Chichester, Brisbane, Toronto, Singapore), 12:555–681 (1992) (no month available).

(List continued on next page.)

*Primary Examiner*—Stanley S. Silverman
*Assistant Examiner*—Sean Vincent
*Attorney, Agent, or Firm*—Dean W. Russell, Esq.; Bruce D. Gray, Esq.; Kilpatrick Stockton L.L.P.

[57] ABSTRACT

A process for determining one or more leachate concentrations of one or more components of a glass composition in an aqueous solution of the glass composition by identifying the components of the glass composition, including associated oxides, determining a preliminary glass dissolution estimator, $\Delta G_p$, based upon the free energies of hydration for the component reactant species, determining an accelerated glass dissolution function, $\Delta G_a$, based upon the free energy associated with weak acid dissociation, $\Delta G_a^{WA}$, and accelerated matrix dissolution at high pH, $\Delta G_a^{SB}$ associated with solution strong base formation, and determining a final hydration free energy, $\Delta G_f$. This final hydration free energy is then used to determine leachate concentrations for elements of interest using a regression analysis and the formula $\log_{10}(N\ C_i(g/L)) = a_i + b_i \Delta G_f$. The present invention also includes a method to determine whether a particular glass to be produced will be homogeneous or phase separated. The present invention is also directed to methods of monitoring and controlling processes for making glass using these determinations to modify the feedstock materials until a desired glass durability and homogeneity is obtained.

35 Claims, 4 Drawing Sheets

OTHER PUBLICATIONS

Jantzen, et al., "Thermodynamic Approach to Glass Corrosion," *Corrosion of Glass, Ceramics and Ceramic Superconductors Principles, Testing, Characterization and Applications,* (Editors: Clark and Zoitos; Published by Noyes Publications, Park Ridge, New Jersey), 6:153–215 (1992) (no month avail).

Jantzen, et al., "Prediction of Glass Durability as a Function of Environmental Conditions," *Mat. Res. Soc. Symp. Proc.,* 125:143–159 (1988) (no month avail).

Jantzen, et al., "Prediction of Glass Durability as a Function of Glass Composition and Test Conditions: Thermodynamics and Kinetics," *Proceedings of the First Intl. Conference on Advances in the Fusion of Glass,* American Ceramic Society, Westerly, Ohio, pp. 24.1–24.17 (1988) (no month avail).

Jantzen, et al., "Prediction of Radioactive Waste Glass Durability by the Hydration Thermodynamic Model: Application to Saturated Repository Environments," *Mat. Res. Soc. Symp. Proc.,* 176:217–228 (1990) (no month avail).

Jantzen, et al., "Pourbaix Diagram for the Prediction of Waste Glass Durability in Geologic Environments," *Mat. Res. Soc. Symp. Proc.,* 112:519–530 (1988) (no month avail).

Jantzen, et al., "Prediction of Nuclear Waste Glass Durability from Natural Analogs," *Advances in Ceramics, Nuclear Waste Management II,* 20:703–712 (1986) (no month avail).

Jantzen, et al., "Nuclear Waste Glass Durability: I, Predicting Environmental Response from Thermodynamic (Pourbaix) Diagrams," *J. of the American Ceramic Society,* 75(9):2433–2448 (9–1992).

Jantzen, et al., "Statistical Process Control of Glass Manufactured for Nuclear Waste Disposal" *The American Ceramic Society Bulletin,* 72(5):55–59, May 1993.

Jantzen, et al., "Thermodynamic Model of Natural Medieval and Nuclear Waste Glass Durability," *J. of Non–Crystalline Solids,* (Elsevier Science Publishers B.V., North Holland Physics Publishing Division), 67:207–223 (1984) (no month available).

Newton and Paul, "A new approach topredicting the durability of glasses from their chemical compositions," *Glass Technology,* 21(6):307–309 (Dec. 1980).

Paul, *Chemistry of Glasses,* (Publishers: Chapman and Hall Ltd., London) pp. 10–12, 14, 20, 21, 23, 25 (1982) (no month available).

Paul, "Chemical Durability of Glass," *Chemistry of Glasses,* (Publishers: Chapman and Hall Ltd., London), pp. 108–147 (1982) (no month avail).

Paul, "Chemical durability of glasses; a thermodynamic approach;" *Journal of Materials Science,* 12:2246–2268 (Dec. 1977).

Plodinec, et al., "Thermodynamic approach to prediction of the stability of proposed radwaste glasses," *Advances in Ceramics, Nuclear Waste Management,* 8:491–495 (1984) (no month available).

Plodinec, et al., "Stability of Radioactive Waste Glasses Assessed from Hydration Thermodynamics," *Scientific Basis for Nuclear Waste Management VII,* (G. L. McVay, Editor; Elsevier Publishers, New York) (755–762 (1984) (no month available).

Postles and Brown, "The DWPF Product Composition Control System at Savannah River: Statistical Process Control Algorithm," *Ceramic Transactions, Nuclear Waste Management IV* (Editors: Wicks, Bickford and Bunnell), The American Ceramic Society, Inc., Westerville, Ohio, 23:559–568 (1991) (no month available).

METHOD OF DETERMINING GLASS DURABILITY

The U.S. government has rights in this invention pursuant to contract no. DE-AC09-89-SR18035 between the U.S. Department of Energy and Westinghouse Savannah River Company.

BACKGROUND OF THE INVENTION

1. Field of the Invention

The present invention relates to glassmaking, more particularly to processes for making glass having certain desired durability characteristics. In some of its embodiments, the present invention relates to processes for making glass that is extremely durable, e.g., glass that is suitable for the encapsulation of radioactive waste material for long term storage in geological waste repositories. In other embodiments, the present invention relates to processes for making glass that, while retaining useful physical properties, will succumb to attack by aqueous fluids, such as fluids present in the lungs, thereby lessening the occurrence of pulmonary or respiratory conditions, carcinogenesis, or asbestosis-like conditions. However, the present invention is generally applicable to other commercial and industrial glassmaking processes.

More specifically, the present invention relates to methods of determining the aqueous leachate concentrations of various components in the glass, based upon the different components present in the glass, and the pH of the aqueous solution of the glass. The methods of the present invention are particularly applicable to determining glass leachate concentrations under expected leaching conditions based upon the feedstock components that are combined to form the glass. As a result, the present invention includes, as one of its aspects, the monitoring and control of the vitrification process.

A particular aspect of the present invention relates to a process for monitoring and controlling vitrification of hazardous waste materials, such as waste sludges, radioactive materials and/or reactor wastes, reactive materials in need of stabilization, spent filter aids, incinerator ash (both municipal and radioactive), incinerator blowdown, contaminated cement or ceramic, ion exchange resins, zeolites, inorganic filter media, asbestos or glass fiber filters, soils or geologic minerals, such as mine tailings, which are to be disposed of or immobilized by vitrification, and particularly by placing the vitrified waste in a long term repository.

Another particular aspect of the present invention relates to the monitoring and control of processes for preparing fiberglass or powdered glass, particularly fiberglass or powdered glass (e.g., "blown in" insulation, short fibers, or other glass powders) desired to be soluble in aqueous solutions such as that present in lung tissue.

2. Description of the Related Art

Glass can be defined as an inorganic product of fusion that has cooled to a rigid condition without crystallizing. Glass has been made and used for thousands of years, and most glass is currently made by processes that convert raw materials at a high temperature to a homogeneous melt, which can then be molded or otherwise formed into desired shapes. Other methods of preparing glasses include solution evaporation, sintering of gels, reactive sputtering, vapor deposition, neutron bombardment, microwave, and shock wave vitrification. A discussion of conventional glassmaking processes is provided in D. C. Boyd et al., Kirk-Othmer Encyclopedia of Chemical Technology, 4th ed., volume 12, pp. 555–627 (1992), the entire contents of which is hereby incorporated by reference, in particular at pages 593–619. Glass, in its various forms, is put to a wide variety of applications, including windows, ultrasonic delay lines, crucibles for growing crystals, and optical systems in analytical devices (vitreous silica); adhesives, cleansers, desiccants, abrasives, cement deflocculants, and surface coatings (sodium silicates); containers, flat glass, pressed and blown ware, and lighting products (soda-lime glasses); laboratory equipment, ovenware, piping, sealed-beam headlights, hazardous and radioactive waste vitrification, and pharmaceutical ampules (borosilicate glasses); airplane windows, frangible containers, lamp envelopes, and flat panel display devices (aluminosilicate glasses); and radiation windows, fluorescent-lamp envelopes, lead crystal, optical glass, artware, and cathode ray tubes (CRT) (lead glasses). Glass is also used in fiber form as insulating material and as a reinforcing material in composites.

Glass durability ranges from highly soluble to highly durable and is dependent on the glass composition and the material to which the glass is exposed. Acids may react with silicate glass to cause a leaching effect or a complete dissolution of the glass. Leaching may occur by a selective exchange of protons in the acid for cations in the glass in a process that is basically diffusion controlled and temperature dependent, and that occurs at a decreasing rate over time. Basic corrosion of silicate glass occurs primarily by dissolution in strong bases (e.g., 5% NaOH solution at 95° C.). However, weaker alkaline solutions may both leach and dissolve glass. Corrosion by water occurs primarily by leaching, although low alkali, high alumina, and borosilicate glasses generally have high resistance to corrosion by water. The highest durability is usually exhibited at neutral pH.

As discussed in Jantzen, "Thermodynamic Approach to Glass Corrosion," in *Corrosion of Glass, Ceramics and Ceramic Superconductors: Principles, Testing, Characterization and Applications,* ed. Clark et al., Noyes Publications (1992), the durability of a glass, e.g., its resistance to corrosion, affects its applicability for various uses. Nevertheless, the corrosion rate of a particular glass in a particular environment has previously been difficult to predict with any reliability. This is, in part, due to the difficulty of directly demonstrating the durability of a man made glass on a geological or historical time scale in a laboratory experiment, and in part due to inadequacies in the predictive value of models of glass durability. The durability of glass is a function of both its kinetic rate of approach to equilibrium and its final thermodynamic equilibrium state in an aqueous environment.

The relationship between glass durability and glass composition is significant to the development of durable commercial glasses and to the development of durable glasses for nuclear waste disposal, as well as to the development of glasses which are soluble in body fluids (e.g., fluids present in lung tissue). Attempts at modeling glass durability based upon composition indicated that durability is a nonlinear function that was highly dependent on the amount of silica and alumina present in the glass matrix and also dependent on the presence of small amounts of additives such as zirconia and titania.

Early kinetic models treated glass leaching as a simple diffusion process; however, more recent kinetic models exist which mathematically describe glass leaching mechanisms in the form of time dependent master equations. Although these models describe the leaching behavior of a given glass, they cannot predict which among a group of glasses will be most durable.

A thermodynamic approach to modeling glass durability that does not require a determination of the time dependent kinetics of the leaching process was first developed by Newton and Paul and is discussed in: Newton and Paul, *Glass Technology*, 21: 307–309 (1980); Paul, *J. Mat. Sci.* 4: 12, 2246–2268 (1977); and Paul, *Chemistry of Glasses*, Chapman & Hall, NY (1982). This approach treats glass as a mixture of species having known free energies of hydration and predicts glass durability from glass composition based upon thermodynamic hydration equations. However, Newton and Paul were unsuccessful in applying their approach to borosilicate glasses and to glasses with varying states of reduction/oxidation. Newton and Paul also did not model any pH dependency of the glass leaching.

Plodinec et al., in "Thermodynamic approach to prediction of the stability of proposed radwaste glasses," in *Advances in Ceramics*, Volume 8: Nuclear Waste Management, pages 491–495 (1984), modified the approach of Newton and Paul to consider explicitly the oxidation state of the glass, thereby expanding the range of applicability of the model to glasses containing iron and manganese.

Jantzen et al., in "Thermodynamic Model of Natural, Medieval and Nuclear Waste Glass Durability," *J. Non-Crystalline Sol.*, 67: 207–223 (1984), further modified the Newton and Paul model to make it more useful with borosilicate glasses by accounting for the free energy effects of the dissociation of silicic acid formed by dissolution of the silica matrix upon exposure to aqueous solutions, in particular alkaline aqueous solutions. This was later extended to more completely account for the dissociation of boric acid formed by dissolution of boria under similar conditions by Jantzen, in "Prediction of Nuclear Waste Glass Durability from Natural Analogs," *Advances in Ceramics*, Volume 20: Nuclear Waste Management II, pp. 703–712 (1986). Jantzen, in "Prediction of Glass Durability as a Function of Glass Composition and Test Conditions: Thermodynamics and Kinetics," *Proceedings of the First Int'l Conference on Advances in the Fusion of Glass*, American Ceramic Society, pp. 24.1–24.17 (1988), suggests the possibility of poorly durable glasses quickly releasing alkali to solution and driving the pH to extremely alkaline conditions, which can accelerate glass matrix dissolution.

Jantzen has also disclosed the use of the free energy of hydration to construct a Pourbaix pH-oxidation potential diagram to help predict the overall nature of the dissolution process and glass durability in "Pourbaix Diagram for the Prediction of Waste Glass Durability in Geologic Environments," *Mat. Res. Soc. Symp. Proc.*, 112: 519–530 (1988), and in "Nuclear Waste Glass Durability: I, Predicting Environmental Response from Thermodynamic (Pourbaix) Diagrams," *J. Am. Ceramic Soc.*, 75(9): 2433–2448 (1992).

As suggested by the above discussion, because of its chemical stability glass has recently been proposed for use as a matrix in which to immobilize hazardous waste, including radioactive waste. In particular, borosilicate glass has been proposed as a stable, permanent medium for the encapsulation and immobilization of radioactive or other hazardous waste, thereby allowing the waste to be disposed of in geological repositories. In one proposed method, discussed in more detail below, glass forming frit and the waste materials to be immobilized are fed into an electric melter, where electric current cause the frit to melt by Joule heating. As the frit melts, and its various ingredients combine, the molten glass can be poured into molds or canisters, where the glass will harden. These molds or canisters can then be placed in a suitable repository for long term disposal or storage.

However, there is a possibility that the repository will, at some point, contain some amounts of groundwater, and that the glass will be exposed to this groundwater after the canisters or cans rust. Such intrusion of groundwater into, and passage through, a repository is considered to be the most likely mechanism by which radionuclides or other immobilized hazardous material may be removed from the waste glass and carried into the biosphere. It is therefore extremely important that the waste glass be stable and durable in the presence of groundwater over geological time scales.

These durability considerations must be balanced against the processing requirements of glass production. In U.S. Pat. No. 5,102,439, Jantzen disclosed a method for controlling a glassmaking process to produce a glass having a viscosity in range that avoids excessive convection during melting and erosion of the melter materials, as well as allowing the glass to be poured. The interplay between durability, viscosity, and liquidus considerations in glassmaking process control is discussed in Postles and Brown, "The DWPF Product Composition Control System at Savannah River: Statistical Process Control Algorithm," *Ceramic Transactions: Nuclear Waste Management IV* 23: 559–568 (1991).

Glass has also been used in fibrous or powdered form for its insulative properties, as well as its strengthening properties in composite materials. However, fibrous or powdered glass is subject to inhalation and has been implicated as a possible causative agent for pulmonary and respiratory problems, including asbestosis and asbestosis-like conditions (silicosis). One approach to solving this problem is to prepare glass fiber or glass powder compositions having increased biosolubility, i.e., increased solubility in fluids likely to be encountered in the lung tissues after the fibers or particles are inhaled. EP 0 588 251 A1 also discloses that control of production processes for preparing such fibers is difficult, as is the maintenance of suitable glass performance characteristics along with biosolubility. EP 0 588 251 A1 discloses that, for those compositions having the desired moisture characteristics, only compositions having enthalpies of formation and calculated free energies of hydration within certain ranges had sufficient performance characteristics to be useful. The enthalpies of hydration are calculated by summing weighted component hydration enthalpies and including a term to account for the free energy of mixing.

SUMMARY OF THE INVENTION

It is an object of the present invention to provide a process for determining the durability and homogeneity characteristics(since durability is affected by glass homogeneity) of a glass based upon its predicted composition and/or the composition of the glass forming feedstock components used to make the glass. It is also an object of the present invention to provide a method of monitoring and/or controlling the composition of glass produced by a large scale (i.e., commercial or industrial scale) glass making process to produce glass having desired durability characteristics, based upon the composition and homogeneity of the glass product or the glass forming feedstock materials.

As pointed out above, it is extremely important that glass containing radioactive or hazardous waste, in particular nuclear waste glass, be stable and durable in the presence of groundwater over geological or historical time scales. This presents challenges for the design and operation of the glassmaking process and for the analysis of the glass produced thereby. Once the nuclear or hazardous waste glass is made, it is difficult or impossible to reformulate or rework it. The glassmaking process must therefore be controlled so that the resulting glass composition is stable under the expected conditions of groundwater contact. Due to the hazardous nature of the material produced, a control scheme that samples the actual product and adjusts operating parameters to modify the product characteristics is insufficient. Accordingly, it is an object of the present invention to select the appropriate process parameters based upon the durability and homogeneity of the glass composition in advance of its actual production. More specifically, it is an object of the present invention to provide a process for determining, in advance, the durability characteristics of the nuclear waste glass based upon the known compositions of the starting materials, and if necessary, adjusting the starting material composition so that the resulting nuclear waste glass will have a suitable durability under the expected storage conditions in the repository.

It is also an object of the present invention to provide a process for monitoring and/or controlling a process for making fiberglass or glass powder so as to obtain a product having sufficient physical and chemical properties to be useful as a fiberglass or glass powder, but also being sufficiently biosoluble and/or phase separated (inhomogeneous) to minimize susceptibility to the development of asbestosis, asbestosis-like conditions, or other pulmonary or respiratory conditions. This can be accomplished in a manner similar to that used for waste glass, i.e., determining the biosolubility characteristics of the glass based upon the known starting materials and adjusting these if necessary to obtain the desired combination of mechanical or chemical properties and biosolubility.

These and other objects and advantages are attained by the present invention by providing a process for determining the durability of a glass composition in an aqueous solution. The process of the present invention allows the determination of the leachate concentration to be done prior to producing the glass composition, based upon an identification of the components of the glass-forming feedstock materials to be fed to a melter, and a prediction of the glass composition and homogeneity derived from this identification of feedstock materials. This allows the leaching characteristics of the resulting glass to be used in the control of the glassmaking process.

Free energies are used in the present invention rather than enthalpies because chemical durability is a chemical process, and the reaction product is related to the free energy ($\Delta G$) rather than the enthalpy ($\Delta H$) of the overall reaction. The more positive the $\Delta G$, the less readily the reaction will occur, and the more negative the $\Delta G$, the more readily the reaction will occur.

The present invention is also directed to a method for determining whether a glass composition will be homogeneous or phase separated by applying a phase separation discriminator function. This determination can be conducted in conjunction with the determination of the aqueous stability discussed above, and the combined determinations may be carried out in any order.

The processes discussed above can be used as part of a process for monitoring production of glass, for instance, by determining the composition of glass-forming feedstock materials to be fed the to a melter, determining a final free energy ($\Delta G_f$) and optionally one or more leachate concentrations of one or more components of a glass composition in an aqueous solution of said glass composition based upon said composition of said glass-forming feedstock materials according to the process discussed above, and comparing this final free energy or at least one of the determined leachate concentrations to an allowable standard for free energy or for that component of the glass composition. This monitoring process can be used in conjunction with other process steps to control the glassmaking operation, for instance, determining whether said difference between said allowable standard for that component in the glass composition and the predicted leachate concentration meets or exceeds a preset value. These monitoring and control processes can also include determination of whether the glass will undergo phase separation (be homogeneous or inhomogeneous), as discussed above.

The present invention also includes a method for preparing a glass that is at least partially soluble in body fluids, such as fluids found in the lung or physiological saline, by determining the relative solubility of the glass in these fluids based upon the glass forming starting materials. This allows processes for making, e.g., fiberglass, to be monitored and controlled to produce glass fibers that are less likely to be implicated in asbestosis, carcinogenesis, or other pulmonary disorders.

The invention summarized above will be more clearly understood from the following description of the drawings and detailed description of the invention. However, these drawings, the description thereof, and the detailed description of the invention are given by way of illustration only, and are not intended, and should not be interpreted, to limit the claims in any way.

BRIEF DESCRIPTION OF THE DRAWINGS

The invention will be more clearly understood, but not limited, by reference to the following drawings, wherein.

DETAILED DESCRIPTION OF SPECIFIC EMBODIMENTS

Figure 1:
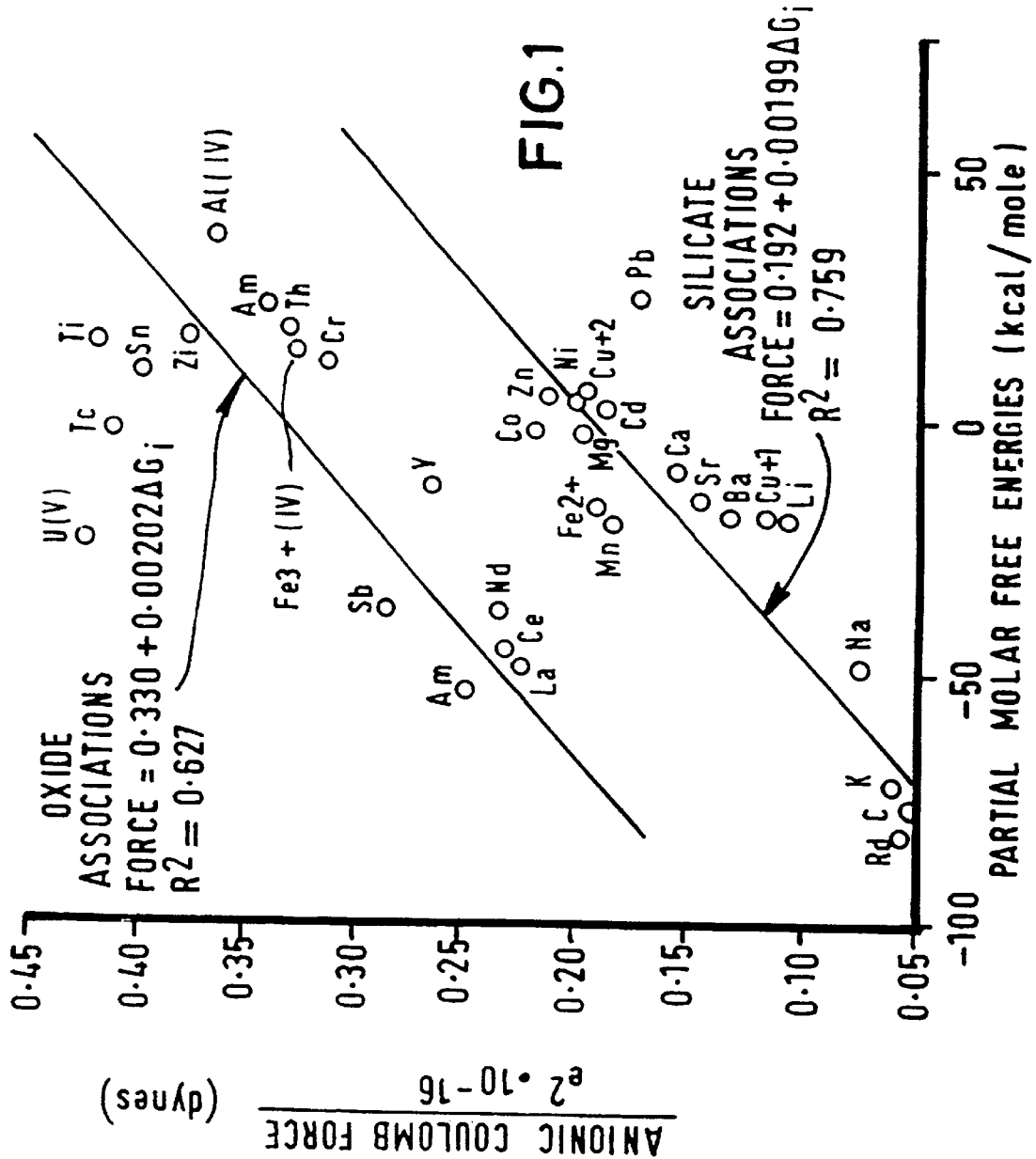
FIG. 1 is a diagram showing the relation between anionic Coulomb force and Partial Molar Free Energies for various cation species in glass.

The present invention is applicable generally to determine glass durability, and to monitor and control glassmaking processes for glasses having a wide range of uses, and prepared using a wide range of feedstocks. More specifically, the present invention is applicable to processes for making glasses which immobilize and encapsulate hazardous or radioactive waste, such as waste sludges, radioactive materials (including both high and low level radioactive wastes, such as reactor wastes), reactive materials requiring stabilization (such as sodium metal), spent filter aids, incinerator ash (both municipal and radioactive), incinerator blowdown, contaminated cement or ceramic, ion exchange resins, zeolite, inorganic filter media, asbestos or glass fiber filters, soils or geological minerals, such as mill tailings, and low level toxins. In some cases (such as with low level radioactive wastes), the vitrified waste materials can safely be reprocessed and sometimes recycled or reused. This reduces or eliminates the need to dispose of or landfill this waste. The process is applicable to the preparation of glasses for the disposal of wastes containing radioactive materials (e.g., U, Th, Cs, Sr, Am, Ce, Nd, La, Co, Tc, Te, or Pu), or hazardous materials (e.g., RCRA materials, such as Ba, As, Cd, Cr, Pb, Se, Ag, Zn, and Ni), or both.

A first step in the process requires determining if a glass meets the criteria in Table I that ensure formation of totally amorphous glasses (i.e., the criteria in the column headed "Most Conservative" in Table I). Next, a preliminary glass dissolution estimator, $\Delta G_p$, is determined from the summation of individual hydration reactions that will occur in the dissolution of the glass composition in the aqueous liquid to which it is exposed. This requires the selection of reactant species in the glass and in the aqueous solution, as well as any gaseous reactant species which might participate in the hydration reaction, such as molecular oxygen and/or carbon dioxide. Hydration product species are also selected, allowing balanced component hydration equations to be written. The partial molar hydration free energies ($\Delta G_i$) of these hydration reactions are then determined, weighted by the mole fraction of the corresponding glass reactant component, and summed to obtain the preliminary glass dissolution estimator.

TABLE I

Proposed Component Limits for Soda-Lime-Silica and Borosilicate Glass Systems

| Component | Component Limit (wt %) | | |
|---|---|---|---|
| | SLS | Borosilicate[1] | Most Conservative[3] |
| $SO_3$ | >0.32 | 0.32 | 0.32 (0.38 as $SO_4$) |
| $P_2O_5$ | >2.5 | 2.1 | 2.1 |
| F | 0.4–0.6 | >0.75 | 0.4–0.6 (0.88–1.32 as NaF) |
| Cl | >0.6 | >0.6 | >0.6 (0.99 as NaCl) |
| I | — | 0.2 | 0.2 |
| $TiO_2$ | — | <1.0[2] | <1.0[2] |
| $Cr_2O_3$ | 0.5 | <0.3 | <0.3[2] |

[1]Borosilicate being defined by ASTM C162 as containing >5 wt % $B_2O_3$.
[2]$TiO_2$ and $Cr_2O_3$ limit based on promotion of crystallization.
[3]Based upon the most conservative values in Table IA below.

TABLE IA

Summary of Component Solubility Limits in Various Glasses Systems.

| Component | Glass Family | Solubility Limit (wt %) |
|---|---|---|
| $SO_3$ | silicate | <1 |
| $SO_3$ | SLS type (low B) | <0.995 |
| $SO_3$ | borosilicate (B >5 wt %) | ~0.995 |
| $SO_3$ | borosilicate | 0.7 ± 0.1 |
| $SO_3$ | borosilicate | 0.6–0.3 |
| $SO_3$ | SLS | 0.1–0.9* |
| $SO_3$ | borosilicate (oxidized) | 0.5–1.0 |
| $SO_3$ | borosilicate (reduced) | 0.15 |
| $SO_4$ | borosilicate | 1.25 |
| $SO_4$ | borosilicate | 1.25 |
| $SO_4$ | borosilicate | 1.2 |
| $SO_4$ | borosilicate | >0.7 |
| $SO_4$ | borosilicate | <0.4 |
| $SO_3$ | alumino-borosilicate (with CaO) | 0.75 |
| $SO_3$ | alumino-borosilicate (no CaO) | 0.47 |
| $SO_3$ | borosilicate | >0.32 |
| $SO_3$ | SLS | >0.32 |
| $P_2O_5$ | borosilicate (low Al) | <2.5 |
| $P_2O_5$ | alumino-silicate (no $B_2O_3$, high CaO and $Al_2O_3$) | 8.0 |

TABLE IA-continued

Summary of Component Solubility Limits in Various Glasses Systems.

| Component | Glass Family | Solubility Limit (wt %) |
|---|---|---|
| $P_2O_5$ | borosilicate | <2.6 |
| $P_2O_5$ | borosilicate | 3.1 ± 0.1 |
| $P_2O_5$ | borosilicate | ~3.0 |
| $P_2O_5$ | borosilicate | <2.5 |
| $P_2O_5$ | borosilicate (with CaO) | 2.1 |
| $P_2O_5$ | alumino-borosilicate (no CaO) | 5.72 |
| $P_2O_5$ | borosilicate | >1.19 |
| $P_2O_5$ | SLS | >2.5 |
| F | Opal | 3 |
| F (as NaF) | SLS | 0.6 (1.32) |
| F (as NaF) | SLS-type (low B, Vycor) | >0.4 (0.88) |
| F | borosilicate | 2.9 ± 0.1 |
| F (as NaF) | SLS and borosilicate | >0.75 (1.66) |
| NaCl | SLS | 2.3 |
| KCl | lead silicate | 1.5 |
| KCl | lead glass | <5.5 |
| NaCl | silicate | 1–5 |
| KCl/NaCl | borosilicate and lead glasses | 1.5–2.0[†] |
| NaCl | borosilicate and lead glass | 1.0[††] |
| Cl | borosilicate | 0.9 ± 0.1 |
| Cl (as NaCl) | SLS and borosilicate | >0.6 (0.99) |
| I | borosilicate | 0.2 |
| $TiO_2$ | soda-titania-silica | 20 |
| $TiO_2$ | borosilicate | <1.0[†††] |
| $Cr_2O_3$ | borosilicate | <0.5 |
| $Cr_2O_3$ | borosilicate | <1.3 |
| $Cr_2O_3$ | borosilicate | <0.3 |
| $Cr_2O_3$ | SLS | ~0.5 |
| $Cr_2O_3$ | SLS (commercial) | 1.5–2.0 |

*$SO_3$ ranges over which glasses tested, no effective solubility limit determined.
[†]Requires a source of $OH^-$ to react with alkali metal chlorides
[††]In the presence of $As_2O_3$, $NO_3$, and trivalent oxides.
[†††]$TiO_2$ limit based on promotion of crystallization, not solubility.

First, the composition of the glass product and the likely hydration reactants are estimated based upon the mole percentage of components present in the feedstock materials. Glass reactant species are chosen with a view toward writing hydration reactions likely to occur between the glass and the aqueous solution. This requires determining whether existing cations in the glass will anionically complex with silica or other oxides. This determination is made by calculating the anionic Coulomb force, $F_c$, as a cation-anion complex (i.e., as a complex of a cation with the $[SiO_4]^{-4}$ anion) according to the formula $$F_c = e^2 \cdot \frac{ZZ'}{(r + r_0)^2}$$

where Z' is the charge on an anion complex, $[SiO_4]^{-4}$, e is the elementary electric charge, Z is the charge on the cation, and r and $r_0$ are the radii of the cation and the anionic $[SiO_4]^{-4}$ group in Ångstroms, respectively. These radii are obtained from published compilations available to those having skill in this art and can be obtained from Tables II and III, below.

The glass reactant species are chosen as the oxide species of cations in the glass structure which are either network formers (ions with high atomic field strengths, calculated as $F=Z/r^2$, where Z is the atomic charge and r is the ionic radius), network modifiers (ions with low atomic field strengths), or intermediate role cations (which can act as either network formers or network modifiers). Network formers are written as oxide species such as $SiO_2$ or $B_2O_3$.

Network modifier cations are written as oxide species which are highly anionically associated with $[SiO_4]^{-4}$ tetrahedra, such as $\{Na_2O+SiO_2\}$. Intermediate role cations are written as oxide species which are not highly anionically associated with $[SiO_4]^{-4}$ tetrahedra, such as $TiO_2$, $Nd_2O_3$, $Fe_2O_3$, and $Al_2O_3$. The choice of glass reactant species assumes that network modifying ions in a glass couple with anionic $[SiO_4]^{-4}$ groups as anionic associations, e.g., an $[SiO_4]^{-4}$ structural group in the glass is ionically bonded to a network modifying ion such as an alkali or alkaline earth metal at the non-bridging oxygen site. These anionic associations are expressed in Table IV below as either $\{MO+SiO_2\}$ or $\{M_2O+SiO_2\}$, where M is any monovalent or divalent species. This provides a consistent manner in which to write hydration reaction equations and avoids assumptions about glass structural components and the different free energies of formation associated with different polymorphic silicate species. In addition, this format is more representative of realistic glass structural models, and provides improved consistency by minimizing structural assumptions.

The Tables II and III below provide measured and/or preferentially predicted valences and atomic radii for a variety of cationic and anionic species in glass. Most of the network modifying oxide species exhibit local coordinations of six or more oxygens. The valences of the cationic species given below are used to determine the oxide component of the anionic association groups for the network modifying hydration equations, e.g., CuO and $Cu_2O$.

The choice of glass reactant species for intermediate glass forming ions and the higher valence ions, such as Al, $Fe^{+3}$, Zr, U, Th, and the rare earths, assumes less dependent coupling between these ions and the $[SiO_4]^{-4}$ tetrahedra in a glass structure. For example, most of these ions exhibit coordination between six or nine oxygens in a glass structure and an intermediate ionic field strength. The valences for the cationic species given in the Table II below are used to determine the oxide reactant species for the intermediate glass component hydration equations used, e.g., FeO and $Fe_2O_3$.

The choice of glass reactant species for the glass forming ions such as B, Si, and P assumes the known covalent bonding of these species with oxygen and the formation of anionic complexes in glass. The valences for the cationic species in the Table II below are used to determine the oxide species of the anionic association groups for the network former hydration equations. Table III below provides both ionic radii and covalent radii for glass forming species expressed as $B_2O_3$, $SiO_2$, and $P_2O_5$.

Metallic melt insolubles are not considered as reactant species. Other species, such as Rh, Pd, Os, Ir, Cu, Sn, and Pt are considered if their glass redox indicates that the species are present as oxides bound ionically in the glass at the oxygen fugacities expected to be encountered during dissolution. If this is the case, these species are considered as glass reactants in a manner similar to that for intermediate glass forming ions (i.e., anionic association groups are not assumed).

As a practical matter, separate reaction equations for network modifiers or intermediate role cations as reactants are written as both associated and unassociated cations, and the partial molar free energies of hydration ($\Delta G_i$) values for each are calculated. Using both the anionic Coulomb force (calculated as discussed above) and the $\Delta G_i$ values, the cation is plotted on FIG. 1. If the cation falls near the straight line in the lower region of FIG. 1 (which represents a plot of the equation $F_c=0.192+0.00199\Delta G_i$), then the reaction equation wherein the cation is a complex with silica is used. If the cation falls near the straight line in the upper region of the FIG. 1 (which represents a plot of the equation $F_c=0.330+0.00202\Delta G_i$), then the reaction equation is used wherein the cation is an oxide.

TABLE II

Coordination, Charge and Ionic Radii for Common Glass Cationic Species[1]

| Element | Coord | Valence | Oxide Species | Ionic Radii[2] Ahrens | Ionic Radii Shannon + Prewitt | Ionic Radii Whittaker |
|---------|-------|---------|---------------|--------------|----------------------|-------------|
| Al | 4 | 3 | $Al_2O_3$ | 0.51 | 0.39 | 0.47 |
| Al | 6 | 3 | $Al_2O_3$ | 0.51 | 0.53 | 0.61 |
| Am | 8 | 4 | $AmO_2$ | 1.07 | 0.95 | 1.03 |
| As | 4 | 3 | $As_2O_3$ | 0.58 | 0.58 | — |
| Ba | 8 | 2 | BaO | 1.34 | 1.42 | 1.50 |
| Ca | 8 | 2 | CaO | 0.99 | 1.35 | 1.20 |
| Cd | 4 | 2 | CdO | 0.97 | 0.80 | 0.88 |
| Ce | 8 | 3 | $Ce_2O_3$ | 1.07 | 1.14 | 1.22 |
| Cm | 6 | 3 | $Cm_2O_3$ | — | 0.98 | 1.06 |
| Co | 4 | 2 | CoO | 0.72 | 0.57 | 0.65 |
| Cr | 6 | 3 | $Cr_2O_3$ | 0.63 | 0.62 | 0.70 |
| Cs | 12 | 1 | $Cs_2O$ | 1.67 | 1.88 | 1.96 |
| Cu | 2 | 1 | $Cu_2O$ | 0.96 | 0.46 | 0.54 |
| Cu | 6 | 2 | CuO | 0.72 | 0.73 | 0.81 |
| Fe | 6H | 2 | FeO | 0.74 | 0.78 | 0.86 |
| Fe | 4H | 3 | $Fe_2O_3$ | 0.64 | 0.49 | 0.63 |
| Fe | 6H | 3 | $Fe_2O_3$ | 0.64 | 0.65 | 0.73 |
| K | 12 | 1 | $K_2O$ | 1.33 | 1.60 | 1.68 |
| La | 9 | 3 | $La_2O_3$ | 1.02 | 1.20 | 1.28 |
| Li | 4, 6 | 1 | $Li_2O$ | 0.68 | 0.59 | 0.68 |
| Mg | 6 | 2 | MgO | 0.66 | 0.72 | 0.80 |
| Mn | 6H | 2 | MnO | 0.80 | 0.83 | 0.91 |
| Mo | 8, 7 | 6 | $MoO_3$ | 0.62 | 0.71 | 0.79[3] |
| Na | 8 | 1 | $Na_2O$ | 0.97 | 1.16 | 1.24 |
| Nd | 8 | 3 | $Nd_2O_3$ | 1.04 | 1.12 | 1.20 |
| Ni | 6 | 2 | NiO | 0.69 | 0.69 | 0.77 |
| Pb | 4 | 2 | PbO | 1.20 | 0.94 | 1.02 |
| Rb | 12 | 1 | $Rb_2O$ | 1.47 | 1.73 | 1.81 |
| Sb | 4 | 3 | $Sb_2O_3$ | 0.76 | 0.77 | 0.85 |
| Se | 6 | 4 | $Se_2O$ | 0.50 | — | — |
| Sn | 6 | 4 | $SnO_2$ | 0.71 | 0.69 | 0.77 |
| Sr | 8 | 2 | SrO | 1.12 | 1.25 | 1.33 |
| Tc | 6 | 4 | $TcO_2$ | — | 0.64 | 0.72 |
| Te | 2, 6 | 4 | $TeO_2$ | 0.7 | 0.52 | 0.60[4] |
| Th | 6 | 4 | $TeO_2$ | 1.02 | 1.00 | 1.08 |
| Ti | 4 | 4 | $TiOI_2$ | 0.68 | 0.61 | 0.69 |
| U | 6 | 4 | $UO_2$ | 0.80 | 1.00 | 1.08 |
| U | 6 | 6 | $UO_3$[1] | 0.97 | 0.73 | 0.81 |
| U | 6 | 4, 6[II] | $U_3O_8$ | — | — | 1.04[5] |
| U | 6 | 4, 6[III] | $U_4O_9$ | — | — | 1.04[5] |
| U | 7 | 5 | $U_3O_8$ | 0.97 | 0.96 | 1.04 |
| Y | 6 | 3 | $Y_2O_3$ | 0.92 | 0.9 | 0.98 |
| Zn | 4 | 2 | ZnO | 0.74 | 0.60 | 0.68 |
| Zr | 6 | 4 | $Z_4O_2$ | 0.79 | 0.72 | 0.86 |

[1]$UO_3$ is considered to be thermodynamically unstable
[II]effective U coordination of 5.33 ($UO_2.2UO_3$)
[III]effective U coordination of 4.5 ($3UO_2.1UO_3$)
[1]All ionic radii are in angstroms, Å.
[2]All Ahrens radii are given for 6 coordination only.
[3]Whittaker radius only given for 7 coordination rather than 8.
[4]Whittaker radius only available for coordination 3 instead of 2 or 6.
[5]The mixture is close to 1.04 Å.

TABLE III

Coordination, Charge and Ionic, Covalent, and Thermochemical Radii for Common Glass Forming Species

| Element | Coord | Charge | Ionic Radii†† Ahrens | Ionic Radii Shannons | Ionic Radii Whittaker | Covalent Radii |
|---------|-------|--------|---------------------|---------------------|----------------------|----------------|
| Al | 4 | 3 | 0.51 | 0.39 | 0.47 | 1.25 |
| B | 4 | 3 | 0.23 | 0.12 | 0.20 | 0.80 |
| B | 3 | 3 | 0.23 | 0.02 | 0.10 | 0.80 |
| P | 4 | 5 | 0.35 | 0.17 | 0.25 | 1.10 |

TABLE III-continued

Coordination, Charge and Ionic, Covalent, and Thermochemical Radii for Common Glass Forming Species

| | | | | | | |
|---|---|---|---|---|---|---|
| Si | 4 | 4 | 0.42 | 0.26 | 0.34 | 1.17 |

| Anionic Complex | Coord | Charge | Thermochemical Radii |
|---|---|---|---|
| $[SiO_4]^{-4}$ | 4 | −4 | 2.42[τ] |

[τ] The measured lattice energy of an $[SiO_4]^{-4}$ tetrahedral group in crystalline species was used to calculate this effective thermochemical radius. The thermochemical radius expresses the degree of ionicity and covalency of the bond, e.g., the thermochemical radius of 2.4 Å for the $[SiO_4]^{-4}$ complex is approximately the sum of the covalent 1.17 Å Si bond and the ionic 1.32 Å oxygen radius.
† All ionic covalent, and thermochemical radii are in angstroms, Å.
†† All Ahrens radii are given for 6 coordination only.

The selection of the aqueous reactant is dependent upon the pH of the aqueous solution to be encountered by the glass composition. In an acidic pH regime (pH<7), $H^+$ should be used as the aqueous reactant. In alkaline pH regimes (pH>7), $OH^-$ or water should be used as the aqueous reactant. In general, in basic pH regimes, the contribution of carbonic acid formed in solution from dissolved $CO_2$ is small enough to be ignored. However, for reaction in carbonate rich groundwater or body (e.g., lung) fluid, the contribution from carbonic acid should be included in the hydration reactions.

If the glass contains reduced species that can be leached therefrom, e.g., $Fe^{+2}$ or $U^{+4}$, molecular oxygen in the aqueous solution will react with the reduced species to oxidize it. As a result, where oxidative dissolution occurs, molecular oxygen should be included as a gaseous reactant. However, if the aqueous solution is devoid of dissolved oxygen, oxidative dissolution will not occur, and oxygen need not be included as a reactant.

Product species for the expected glass hydration reactions must also be selected before hydration reaction equations can be written. These are selected using Pourbaix pH—potential (pH-Eh) diagrams available in the art (e.g., in M. Pourbaix, *Atlas of Electrochemical Equilibria in Aqueous Solutions,* English translation of 1966, French version by J. A. Franklin (Ed)., National Association of Corrosion Engineers, Houston, Tex. (1974); D. G. Brookins, *Eh-pH Diagrams for Geochemistry*, Springer-Verlag, New York (1988)) to predict the stability of aqueous and solid product species at equilibrium under the expected pH and Eh environmental conditions of the solution. For example, in an expected oxidized basic leachate environment, the Eh and pH of the environment are plotted, and the stable aqueous, hydroxide, and hydrous oxide species predicted by the Pourbaix diagrams are selected as $\Delta G_i$ product species.

Once reactant and product species are selected, a chemically and electrically balanced hydration reaction for each glass component is written, and the partial molar hydration free energy for each reaction is calculated according to the equation $\Delta G_i = \Delta G_{(products)} - \Delta G_{(reactants)}$. The most common hydration reactions in an aqueous oxidized basic environment, together with their partial molar hydration free energies and relevant pH range, are provided below in Table IV.

TABLE IV

Primary Basis Set of Partial Molar Hydration Free Energies, $\Delta G_i$, for Glass in Oxidized pH Regimes†

| Hydration Reactions | $\Delta G_i$ (kcal/mole) | pH Range |
|---|---|---|
| $Al_2O_3 + H_2O \leftrightarrow 2AlO_2^- (aq) + 2H^+ (aq)$ | +37.68 | 7–14 |
| $AmO_2 + 3H_2O \leftrightarrow Am(OH)_5^- (aq) + H^+ (aq)$ | +23.92 | 7–14 |
| $As_2O_3 + 3H_2O + O_2 \leftrightarrow 2HAsO_4^{-2} (aq) + 4H^+ (aq)$ | −33.65[1] | 7–11 |
| $B_2O_3 + 3H_2O \leftrightarrow 2H_3BO_3 (aq)$ | −10.43 | 7–10 |
| $\{BaO + SiO_2\} + 2H_2O \leftrightarrow Ba(OH)_2 + H_2SiO_3 (aq)$ | −19.13 | 7–14 |
| $\{CaO + SiO_2\} + 2H_2O \leftrightarrow Ca(OH)_2 + H_2SiO_3 (aq)$ | −9.74 | 7–14 |
| $\{CdO + SiO_2\} + 2H_2O \leftrightarrow Cd(OH)_2 + H_2SiO_3 (aq)$ | +2.31 | 7–14 |
| $Ce_2O_3 + 3H_2O \leftrightarrow 2Ce(OH)_3$ | −44.99[2] | 7–14 |
| $\{CoO + SiO_2\} + \frac{5}{2}H_2O + \frac{1}{4}O_2 \leftrightarrow Co(OH)_3 + H_2SiO_3 (aq)$ | −2.33[3] | 7–14 |
| $Cr_2O_3 + 3H_2O \leftrightarrow 2Cr(OH)_3$ | +11.95[4] | 7–14 |
| $\{Cs_2O + SiO_2\} + 2H_2O \leftrightarrow 2Cs^+ (aq) + 2OH^- (aq) + H_2SiO_3 (aq)$ | −76.33 | 7–14 |
| $\{Cu_2O + SiO_2\} \frac{1}{2}O_2 + 3H_2O \leftrightarrow 2Cu(OH)_2 + H_2SiO_3 (aq)$ | −18.85[5] | 7–14 |
| $\{CuO + SiO_2\} + 2H_2O \leftrightarrow Cu(OH)_2 + H_2SiO_3 (aq)$ | +5.59 | 7–14 |
| $\{FeO + SiO_2\} + \frac{1}{4}O_2 + \frac{5}{2}H_2O \leftrightarrow Fe(OH)_3 + H_2SiO_3 (aq)$ | −17.28 | 7–14 |
| $Fe_2O_3 + 3H_2O \leftrightarrow 2Fe(OH)_3$ | +14.56 | 7–14 |
| $\{K_2O + SiO_2\} + 2H_2O \leftrightarrow 2K^+ (aq) + 2OH^- (aq) + H_2SiO_3 (aq)$ | −72.36 | 7–14 |
| $La_2O_3 + 3H_2O \leftrightarrow 2La(OH)_3$ | −48.59 | 7–14 |
| $\{Li_2O + SiO_2\} + 2H_2O \leftrightarrow 2Li^+ (aq) + 2OH^- (aq) + H_2SiO_3 (aq)$ | −19.99 | 7–14 |
| $\{MgO + SiO_2\} + 2H_2O \leftrightarrow Mg(OH)_2 + H_2SiO_3 (aq)$ | −2.52 | 7–14 |
| $\{MnO + SiO_2\} + \frac{1}{2}O_2 + H_2O \leftrightarrow Mn(OH)_2 + H_2SiO_3 (aq)$ | −20.39[6] | 7–14 |
| $MoO_3 + H_2O \leftrightarrow 2H^+ (aq) + MoO_4^{-2} (aq)$ | +16.47[7] | 7–14 |
| $\{Na_2O + SiO_2\} + 2H_2O \leftrightarrow 2Na + (aq) + 2OH^- (aq) + H_2SiO_3 (aq)$ | −49.04 | 7–14 |
| $Nd_2O_3 + 3H_2O \leftrightarrow 2Nd(OH)_3$ | −37.79 | 7–14 |
| $\{NiO + SiO_2\} + 2H_2O \leftrightarrow Ni(OH)_2 + H_2SiO_3 (aq)$ | +4.42[8] | 7–14 |
| $P_2O_5 + 3H_2O \leftrightarrow 2HPO_4^{-2} (aq) + 4H^+ (aq)$ | −26.55 | 7–12 |
| $\{PbO + SiO_2\} + 2H_2O \leftrightarrow NPbO_2^- (aq) + H_2SiO_3 (aq) + H^+ (aq)$ | +25.10 | 7–14 |
| $PuO_2 + 3H_2O \leftrightarrow Pu(OH)_5^- (aq) + H^+ (aq)$ | +30.75 | 7–14 |
| $\{Rb_2O + SiO_2\} + 2H_2O \leftrightarrow 2Rb^+ (aq) + 2OH^- (aq) + H_2SiO_3 (aq)$ | −82.18 | 7–14 |
| $RuO_2 + \frac{1}{2}O_2 + H_2O \leftrightarrow RuO_4^- (aq) + 2H^+ (aq)$ | +57.30[9] | 7–10 |
| $Sb_2O_3 + O_2 + H_2O \leftrightarrow 2SbO_3^- (aq) + 2H^+ (aq)$ | −37.56[10] | 7–14 |
| $SeO_2 + \frac{1}{2}O_2 + H_2O \leftrightarrow SeO_4^{-2} (aq) + 2H^+ (aq)$ | −7.8[11] | 7–14 |
| $SiO_2 + H_2O \leftrightarrow H_2SiO_3 (aq)$ | +4.05 | 7–10 |
| $SnO_2 + 2H_2O \leftrightarrow Sn(OH)_4$ | +10.16[12] | 7–12 |

TABLE IV-continued

Primary Basis Set of Partial Molar Hydration Free Energies, $\Delta G_i$, for Glass in Oxidized pH Regimes[†]

| Hydration Reactions | $\Delta G_i$ (kcal/mole) | pH Range |
|---|---|---|
| {SrO + SiO$_2$} + H$_2$O ↔ Sr(OH)$_2$ + H$_2$SiO$_3$ (aq) | −15.67 | 7–14 |
| TcO$_2$ + ½O$_2$ + H$_2$O ↔ TcO$_4^-$ (aq) + 2H$^+$ (aq) | −2.04 | 7–14 |
| TeO$_2$ + ½O$_2$ + H$_2$O ↔ TeO$_4^{-2}$ (aq) + 2H$^+$ (aq) | +12.02 | 7–14 |
| ThO$_2$ + H$_2$O ↔ Th(OH)$_4$ | +19.23 | 7–14 |
| TiO$_2$ + H$_2$O ↔ TiO(OH)$_2$ | +16.27[13] | 7–14 |
| U$_3$O$_8$ + ½O$_2$ + 6H$_2$O ↔ 3(UO$_3$.2H$_2$O) | −23.77[14] | 7–14 |
| Y$_2$O$_3$ + 3H$_2$O ↔ 2Y(OH)$_3$ | −12.91 | 7–14 |
| {ZnO + SiO$_2$} + 2H$_2$O ↔ Zn(OH)$_2$ + H$_2$SiO$_3$ (aq) | +4.97 | 7–14 |
| ZrO$_2$ + H$_2$O ↔ HZrO$_3^-$ (aq) + H$^+$ (aq) | +17.49 | 7–14 |

[†]Note silver (Ag) and gold (Au) are omitted since Au is metallic at all oxygen fugacities and glass redox conditions while Ag is 90–98% metallic at oxygen fugacities and glass redox values (i.e., Fe$^{+2}$/Fe$^{+3}$ between 0.05 the analytic detection limit to 0.22 for the EA glass) anticipated at the melt temperatures and conditions anticipated in waste glass melters.
[1]As$^{3+}$ is predicted to be the dominant (50–95%) glass reactant species at the glass redox values anticipated in waste glass melters, As$^{5+}$ as As$_2$O$_5$ decomposes at temperatures of 1100° C. and is not expected to occur as a glass oxide species.
[2]Ce$^{3+}$ is predicted to be the dominant (70–90%) glass reactant species at the glass redox values anticipated in waste glass melters.
[3]Co$^{2+}$ is predicted to be the dominant (>98%) glass reactant species at the glass redox values anticipated in waste glass melters.
[4]Cr$^{3+}$ is predicted to be the dominant (90–100%) glass reactant species at the glass redox values anticipated in waste glass melters.
[5]Cu$^+$ is predicted to be the dominant (35–80%) glass reactant species at the glass redox values anticipated in waste glass melters.
[6]Mn$^{3+}$ is predicted to be the dominant (90–100%) glass reactant species at the glass redox values anticipated in waste glass melters.
[7]Mo$^{6+}$ is predicted to be the dominant (100%) glass reactant species at the glass redox values anticipated in waste glass melters.
[8]Ni$^{+2}$ is predicted to be the dominant (>99%) glass reactant species at the glass redox values anticipated in waste glass melters.
[9]Although RuO is present in glass as an oxide at the glass redox values anticipated in waste glass melters, RuO$_2$ is melt insoluble and should not be included in the calculation of a free energy of hydration function for glass.
[10]Sb$^{+3}$ is predicted to be the dominant (90–100%) glass reactant species at the glass redox values anticipated in waste glass melters.
[11]Se$^{+4}$ is predicted to be the dominant (95–100%) glass reactant species at the glass redox values anticipated in waste glass melters.
[12]Sn$^{+4}$ is predicted to be the dominant (100%) glass reactant species at the glass redox values anticipated in waste glass melters.
[13]Ti$^{+4}$ is predicted to be the dominant (100%) glass reactant species at the glass redox values anticipated in waste glass melters.
[14]Mixed U valence is predicted to be the dominant (0–10% U$^{+4}$, 10–50% U$^{+5}$ and 40–90% U$^{+6}$) glass reactant species at the glass redox values anticipated in waste glass melters since UO$_3$ is considered to be thermodynamically unstable and the effective U coordination of U$_3$O$_8$ is 5.33 (UO$_2$.2UO$_3$), while the effective U coordination of U$_4$O$_9$ is 4.5 (3UO$_2$.1UO$_3$), U$_3$O$_8$ was chosen as the most likely glass reactant species at the glass redox values anticipated in waste glass melters.

Examples of hydration equations useful when $CO_2$ is a significant factor in acidic and basic pH regimes, or when oxidative dissolution of reduced species cannot occur, or when an acidic pH regime is encountered, together with the associated partial molar hydration free energies and pH ranges are given below:

The partial molar hydration free energy for each hydration reaction written for the reactant and product species determined above is weighted by the mole fraction of the corresponding associated and non-associated glass reactant species in the glass composition. The weighted free energies are then summed to obtain a preliminary free energy of

| Hydration Reactions | $\Delta G_i$ (kcal/mole) | pH Range |
|---|---|---|
| CO$_2$ Option Examples for Acidic and Basic pH Regimes | | |
| Na$_2$O + SiO$_2$ + H$_2$CO$_3$ ↔ 2Na$^+$ + H$_2$SiO$_2$ + CO$_3^{-2}$ | −10.76 | 0–7 |
| Na$_2$O + SiO$_2$ + H$_2$CO$_3$ + + H$_2$O ↔ 2Na$^+$ + H$_2$SiO$_3$ + HCO$_3^-$ + OH$^-$ | −59.44 | 7–10 |
| Eh Option Examples Without Oxidative Dissolution | | |
| FeO + SiO$_2$ + 2H$_2$O ↔ Fe(OH)$_2$ + H$_2$SiO$_3$ | +6.45 | 7–14 |
| MnO + SiO$_2$ + 2H$_2$O ↔ Mn(OH)$_2$ + H$_2$SiO$_3$ | −0.13 | 7–13 |
| H+ Option Examples | | |
| Na$_2$O + SiO$_2$ +2H$^+$ ↔ 2Na$^+$ + H$_2$SiO$_3$ | −87.22 | 0–7 | hydration, or preliminary glass dissolution estimator, $\Delta G_p$. While not wishing to be bound by any theory, we believe that this preliminary glass dissolution estimator accounts for the dissolution effects occurring due to: (1) ion exchange between cations in the glass matrix and protons in the aqueous solution; (2) matrix dissolution, wherein siloxane bonds forming the glass matrix are attacked and broken by hydroxyl ions in the solution; and (3) surface layer formation, wherein certain species in the solution cause nucleation of precipitated amorphous or crystalline species on the glass surface exposed to the aqueous solution.

An accelerated glass dissolution function is also determined in order to account for the free energy effects of dissociation of weak acids in basic aqueous solution, e.g., the dissociation of silicic and/or boric acid formed in the aqueous solution by dissolution of the silica and boria matrices in strong base, and for the free energy effects of accelerated matrix dissolution, i.e., the increased removal of silica and/or boria resulting from an increase in the activity of the hydroxyl ion in a strongly basic solution.

The silica and boria matrices in the glass composition dissolve into silicic acid and boric acid, respectively, and then dissociate in strong base according to the following equations:

$$M_2O + SiO_2 + 2H_2O \leftrightarrow 2M^+ + 2OH^- + H_2SiO_3$$

$$H_2SiO_3 + OH^- \leftrightarrow HSiO_3^- + H_2O$$

$$HSiO_3^- + OH^- \leftrightarrow SiO_3^{-2} + H_2O$$

$$B_2O_3 + 3H_2O \leftrightarrow 2H_3BO_3$$

$$2H_3BO_3 + 2OH^- \leftrightarrow 2H_2BO_3^- + 2H_2O$$

$$2H_2BO_3^- + 2OH^- \leftrightarrow 2HBO_3^{-2} + 2H_2O$$

$$2HBO_3^{-2} + 2OH^- \leftrightarrow 2BO_3^{-3} + 2H_2O$$

The pH expected to exist in the solution of the glass composition is first determined by one of several methods, e.g., (1) a stepwise regression of tested leachate pH vs. molar glass composition, (2) a linear fit of $\Delta G_p$ to measured pH, (3) a linear fit of solution pH to glass composition in terms of molar excess strong base components (expressed as the ratio $[SB]_{glass}/[WA]_{glass}$, where $[SB]_{glass}$ is the molar strong base concentration available in the glass (e.g., $Li_2O$, $Na_2O$, and $K_2O$ in the glass capable of forming $OH^-$ by hydrolysis) and $[WA]_{glass}$ is the molar weak acid concentration available in the glass (e.g., $SiO_2$ and $B_2O_3$ in the glass capable of hydrolyzing to form silicic or boric acid)), or (4) measuring the pH. An example of each method is provided below.

(1) Based upon such a regression of leachate pH vs. molar glass composition, the pH can be determined from a formula such as that shown below:

$pH_{det}$ = $-3.81[Al_2O_3] - 2.82[B_2O_3] - 219.88[BaO] + 215.82[CuO] + 2.74[FeO] - 5.36[K_2O] + 6.74[Li_2O] + 6.30[MnO] + 12.47[Na_2O] + 113.12[SrO] + 25.42[TiO_2] - 25.67[ZnO] - 7.58$ (accuracy $R^2 = 0.85$).

(2) Based upon a linear fit of $\Delta G_p$ to measured pH, for all pH>9.5, the pH can be determined from the formula:

$pH_{det} = 8.781 - 0.17854 \Delta G_p$ (accuracy $R^2 = 0.61$).

(3) Based upon a linear fit of solution pH to molar excess strong base components in the glass composition, expressed as the ratio $[SB]_{glass}/[WA]_{glass}$, the pH can be determined from the formula:

$pH_{det} = 7.03 + 6.87 [SB]_{glass}/[WA]_{glass}$ (accuracy $R^2 = 0.67$).

(4) By measuring the pH ($pH_{meas}$), the accuracy obtained is indicated by $R^2 = 0.86$.

A term accounting for the free energy effects of the above silicic acid and boric acid dissociation reactions is determined based upon the above pH determination for the aqueous solution of the glass composition, using the following formula:

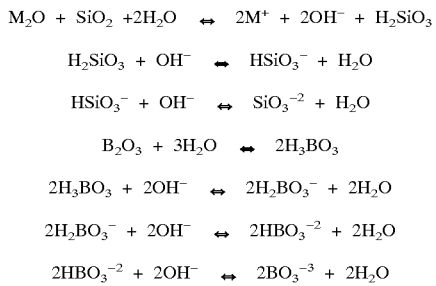

wherein $pH_{det}$ is said determined pH of said aqueous solution of said glass composition.

Accelerated matrix dissolution occurs when the concentration of excess strong base in the leachate exceeds the buffer capacity of the weak acids in solution, i.e., the moles of strong base are greater than the moles of weak acid. This causes the leachate pH to rise and the stability of the product species for the partial molar hydration energy equations used to determine $\Delta G_p$ to change. As a result, for pH values higher than 11, pH dependent $\Delta G_i$ values must be derived for the accelerated attack of the high pH solutions on the residual glass matrix. The reactions used can be determined by writing buffer couple reactions for silica and boria hydration, e.g.:

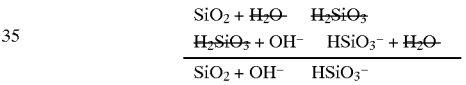

When the buffer couple equations are constructed for the most common hydration reactions in strong base for the various species undergoing accelerated dissolution, the following Table V is obtained.

TABLE V

| | $\Delta G_i$ (kcal/mole) | pH Range |
|---|---|---|
| $SiO_2 + OH^-_{(aq)} \leftrightarrow HSiO_3^-_{(aq)}$ | −1.5 | 11–12 |
| $SiO_2 + 2OH^-_{(aq)} \leftrightarrow SiO_3^{-2}_{(aq)} + H_2O$ | −2.82 | 12–14 |
| $B_2O_3 + H_2O + 2OH^-_{(aq)} \leftrightarrow 2H_2BO_3^-_{(aq)}$ | −23.37 | 11–12.5 |
| $B_2O_3 + 4OH^-_{(aq)} \leftrightarrow 2HBO_3^{-2}_{(aq)} + H_2O$ | −24.29 | 12.5–13.5 |

TABLE V-continued

| | $\Delta G_i$ (kcal/mole) | pH Range |
|---|---|---|
| $B_2O_3 + 6OH^-_{(aq)} \leftrightarrow 2BO_3^{-3}_{(aq)} + 3H_2O$ | −24.85 | >13.5 |
| $RuO_2 + 1/2\, O_2 + H_2O \leftrightarrow RuO_4^{-2}_{(aq)} + 2H^+_{(aq)}$ | +43.80 | 11–14 |

TABLE V-continued

| | $\Delta G_i$ (kcal/mole) | pH Range |
|---|---|---|
| $TeO_2 + 2H_2O \leftrightarrow HTeO_4^-{}_{(aq)} + 3H^+{}_{(aq)}$ | +54.54 | 11–14 |
| $P_2O_5 + H_2O + 2OH^-{}_{(aq)} \leftrightarrow 2PO_4^{-3}{}_{(aq)} + 4H^+$ | −31.07 | 12–14 |
| $SnO_2 + H_2O \leftrightarrow SnO_3^{-2}{}_{(aq)} + 2H^+{}_{(aq)}$ | +43.55 | 12–14. |

These pH dependent partial molar hydration energies are also weighted by the mole fraction of the reactant component in the glass composition and summed to obtain $\Delta G_a^{SB}$. This can conveniently be done in three steps: in the first step, the weighted free energies for reactions occurring at pH>11 are summed; in the second step, the weighted free energies for reactions occurring pH>12 are summed; and in the third step, the free energies from the first two steps are summed.

Because the $\Delta G_a^{WA}$ value is calculated in units of kcal/mol glass, it must be converted to units of kcal/100 g by multiplying by a factor of $$\left(\frac{100}{MW}\right)$$

where MW is the molecular weight of the glass, and can be estimated by the formula:

$$\left(\frac{100}{MW}\right) = \sum_{all}\left(\frac{x_i}{M_i}\right)$$

where $x_i$ is the percent by weight and $M_i$ is the molecular weight of the $i^{th}$ oxide. This is contrary to the procedure followed in prior methods, wherein the free energy has been normalized.

The $\Delta G_a$ function is then calculated by summing the terms $$\left(\frac{100}{MW}\right)\Delta G_a^{WA}$$

$\Delta G_a^{WA}$ and $\Delta G_a^{SB}$.

A final free energy of hydration, $\Delta G_f$, is then determined by summing the terms $\Delta G_p$ and $\Delta G_a$. This final free energy of hydration can then be used to determine the durability of the glass composition in contact with the leachate solution. For example, a graphical or mathematical correlation between the final free energy and normalized leachate concentrations for various species or elements in the glass can be used to determine the expected concentrations of elements of interest in the glass released to solution, using a correlation of the form:

$$\log_{10}(N\ C_i(g/L)) = a_i + b_i \Delta G_f$$

wherein N $C_i$ is the normalized release of element i in grams of glass per liter of aqueous solution, $C_i$ is the concentration of element i in the solution in grams of i per liter, and $a_i$ and $b_i$ are constants for a particular element. The term N $C_i$ can be used to determine $C_i$ according to the formula $$NC_i = \frac{C_i}{F_i}$$

wherein $F_i$ is the weight fraction of element i in the glass, in grams of element i per grams of glass.

As an example, the expected concentrations of elements having maximum allowable leachate concentrations imposed by relevant regulations can be determined by determining the final free energy of hydration using the process disclosed above, and then using a correlation to obtain the expected leachate concentration, which can then be compared to the regulatory standard. For instance, elements that are required to be monitored by the Waste Acceptance Product Specifications (WAPS) applicable to the Defense Waste Processing Facility (DWPF) at the Savannah River Site (SRS) include B, Li, and Na. The correlations for these elements, as well as for Si (for comparison purposes), together with the relevant $R^2$ values, are given below:

$$\log_{10}[N\ C_B(g/L)] = -1.535 - 0.104\ \Delta G_f\quad R^2 = 0.86$$

$$\log_{10}[N\ C_{Li}(g/L)] = -1.249 - 0.0847\ \Delta G_f\quad R^2 = 0.84$$

$$\log_{10}[N\ C_{Na}(g/L)] = -1.448 - 0.0981\ \Delta G_f\quad R^2 = 0.88$$

$$\log_{10}[N\ C_{Si}(g/L)] = -1.424 - 0.0762\ \Delta G_f\quad R^2 = 0.84$$

By way of comparison, correlations between N $C_i$ and $\Delta G_p$ yield the following expressions and $R^2$ values:

$$\log_{10}[N\ C_B(g/L)] = -1.901 - 0.181\ \Delta G_p\quad R^2 = 0.77$$

$$\log_{10}[N\ C_{Li}(g/L)] = -1.546 - 0.147\ \Delta G_p\quad R^2 = 0.75$$

$$\log_{10}[N\ C_{Na}(g/L)] = \mathbf{-1.801 - 0.171}\ \Delta G_p\quad R^2 = 0.80$$

$$\log_{10}[N\ C_{Si}(g/L)] = \mathbf{-1.663 - 0.129}\ \Delta G_p\quad R^2 = 0.72$$

These $R^2$ values are substantially smaller than those obtained for correlations using $\Delta G_f$, and the correlations using $\Delta G_p$ are truly nonlinear. Thus, the use of $\Delta G_f$ to determine the expected leachate concentration provides a more accurate result, particularly for situations where the glass is expected to be exposed to neutral to basic aqueous conditions in a geologic repository.

Alternatively, in another embodiment of the invention, a series of $\Delta G_f$ values for glasses of known stability under the expected leachate conditions could be developed, and the $\Delta G_f$ values obtained by the present method compared to this series. If the obtained $\Delta G_f$ value corresponds to that of a glass known to be stable under the expected leachate conditions, then the glassforming materials can be allowed to proceed to the melter. If the obtained value does not correspond to a glass known to be stable under the expected leachate conditions, then the feedstock materials can be modified as discussed below.

In a further embodiment of the invention, it is possible to determine a value for $\Delta G_f$ without first determining the pH of the leachate solution. In this embodiment, hydration reactions are written for the reactant and product species expected in the expected pH range of the leachate solution, and the partial molar hydration free energy changes ($\Delta G_i$) associated with those reactions are weighted by the mole fractions of the oxide species (including associated glass components) to obtain a Preliminary Free Energy of Hydration, $\Delta G_p$, as discussed above. For $\Delta G_p$ values that are more negative than −7.5 kcal/mole, accelerated glass dissolution occurs when the glass composition drives the leachate pH to exceed values of around 10, e.g., when the concentration of excess strong base in the leachate exceeds the buffer capacity of the weak acids in solution. If the $\Delta G_p$ for a glass is more positive than −7.5 kcal, then the relationship between log $NC_i$ and $\Delta G_p$ is linear. If the $\Delta G_p$ for a glass is more negative than −7.5 kcal then the relationship is non-linear. To account for this, an accelerated glass dissolution parameter, $\Delta G_a$, can be estimated by assuming that every mole of $H_2SiO_3$ formed by hydration of alkali or alkaline earth oxides in glass undergoes dissociation, according to the following overall accelerated dissolution reactions:

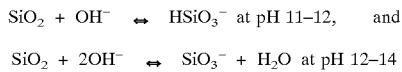

Similarly, the dissociation of boron species in the glass can be assumed to follow the reactions:

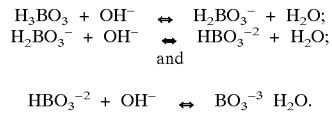

A value for $\Delta G_a$ is then calculated by multiplying the partial molar free energy, $\Delta G_i$, for each of these reactions by the mole fraction of the structurally associated silicate and oxide, and summing the products, in a manner similar to that described above.

For glasses having a $\Delta G_p$ in the range between −9.5 kcal/mole and −7.5 kcal/mole, the first dissociation reactions make the largest impact on $\Delta G_a$. When $\Delta G_p$ is more negative than −9.5 kcal/mole, the $\Delta G_a$ term includes an additional component resulting from additional dissociation reactions.

Another aspect of predicting glass durability involves the prediction of whether a glass will be homogeneous or will undergo phase separation. Phase separation in glasses generally takes the form of two immiscible glass phases which differ in chemical composition and surface tension. Separation into two phases may have various causes, but the final result is that the original structurally homogeneous glass is separated into two or more vitreous (amorphous, noncrystalline) phases of different density, i.e., glass-in-glass phase separation. Morphologically, glass-in-glass phase separation may take the form of droplets or channels of various dimensions which have defined boundaries. Visual observation of glass-in-glass phase separation will only be possible in an electron microscope if the size of the glass-in-glass phase separation is sufficiently large and/or the densities of the two glasses are sufficiently different that the phase boundaries are well defined. Glasses can also phase separate by spinodal decomposition, which is separation of the two phases as sinusoidal composition fluctuations at the 20 to 200 Å size. In the early stages, the composition fluctuations have diffuse boundaries which often cannot even be seen under electron microscopy. These boundaries sharpen during the later stages of spinodal decomposition approximating the sharper boundaries of phases which separate by a nucleation and growth mechanism.

Phase separation is of concern because one of the immiscible phases is always more soluble than the other, causing the overall durability of phase separated glasses to be poorer than for a homogeneous glass of the same composition. Because the amount of phase separation in a given glass is a strong function of the thermal history and/or heat treatment to which a glass is subjected, the extent of phase separation can only be controlled during production of glass if the thermal history and/or heat treatment is controlled. The present invention includes a method of determining in advance whether a particular glass composition can be expected to be phase separated, or homogeneous. This allows for control of the thermal history to avoid phase separation in processes where such control is possible. In processes where such thermal control is not possible, the present invention provides a method for determining whether phase separation will occur, in order to modify the feedstock composition so that the resulting glass will no longer be expected to undergo phase separation.

The determination of whether a particular glass composition (to be prepared) is likely to undergo phase separation or is likely to be homogeneous is made by the application of a phase separation discriminator function. First, a flit component function, x, is determined to be the sum of all sources of alkali species (including alkali species introduced in the glass frit, waste, etc.) and $B_2O_3$ and $SiO_2$, in percent by weight based upon the sum of these components in the resulting glass. Next, a sludge component function, y, is determined to be the sum of $Al_2O_3$, $Fe_2O_3$, FeO calculated as $Fe_2O_3$, $Nd_2O_3$, $Ce_2O_3$, $La_2O_3$, $Y_2O_3$, CaO, and $MoO_3$, in percent by weight based upon the sum of these components in the resulting glass, The glass composition formed by the melter will be homogeneous if the following inequality is satisfied.

$$-1.6035\ x - 5.6478\ y + 210.9203 < 0.$$

If this inequality is not satisfied, then the glass composition may be phase separated if the thermal history is not controlled. If the glass being produced is a radioactive or hazardous waste glass, then a homogeneous glass will be necessary. If the glass being produced is to be used in applications requiring biosolubility, then phase separation is desirable.

Figure 2:
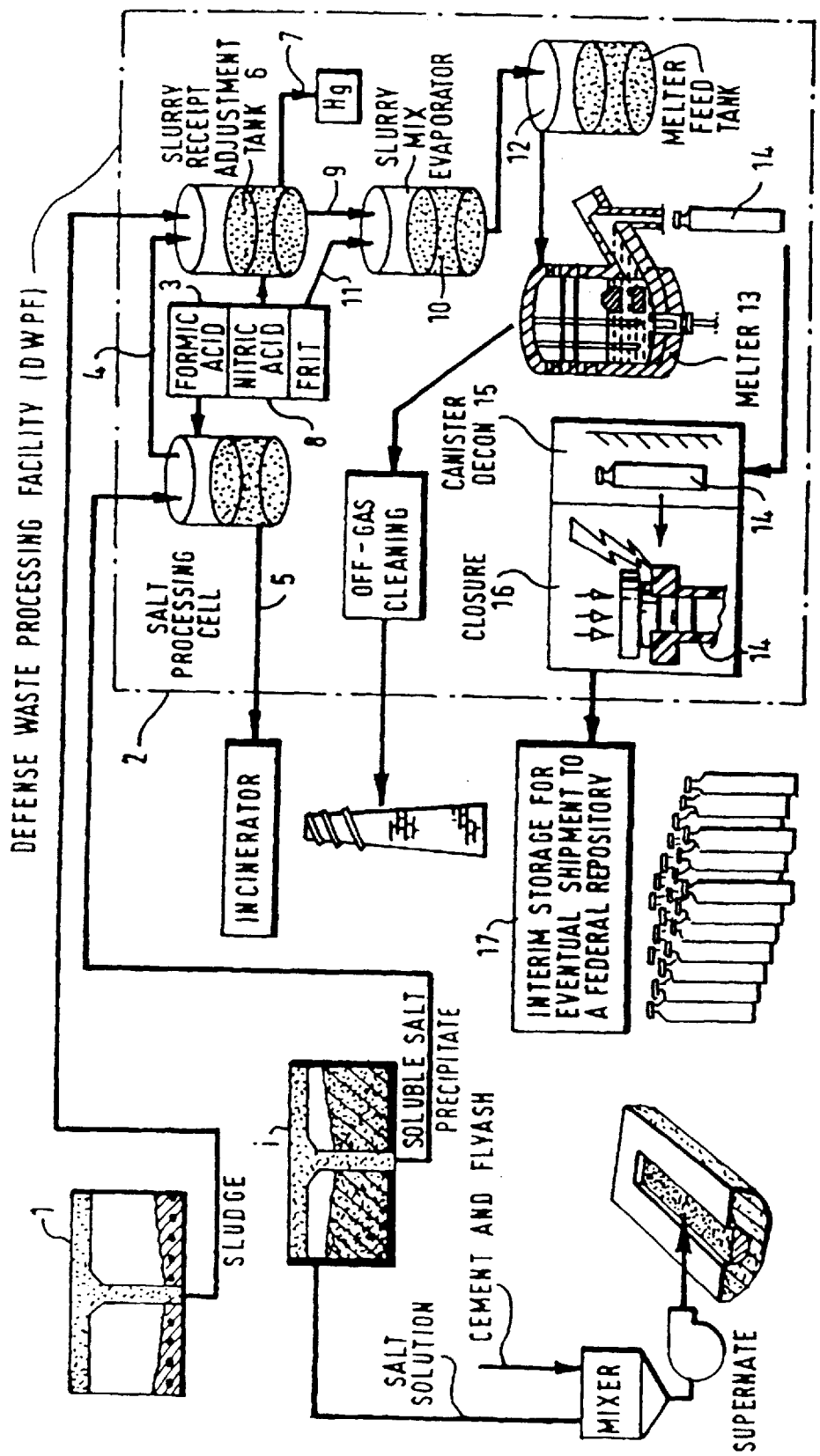
FIG. 2 is a schematic diagram of a process for producing high level nuclear waste glass.

An illustrative embodiment of the present invention, which is mentioned above, involves its use in producing high level nuclear waste glass at SRS, shown in FIG. 2. Liquid, high level nuclear waste that has accumulated from over 35 years of reprocessing nuclear fuels for defense purposes is immobilized in borosilicate glass at the DWPF. In this process, a ceramic, slurry fed, Joule-heated electric melter produces borosilicate nuclear waste glass melts at approximately 1150° C. This melt is poured into stainless steel canisters for eventual disposal in a geological waste repository.

More specifically, high level radioactive wastes produced by the defense industry were initially acidic and were neutralized with NaOH so that they could be safely stored in carbon steel tanks while a solidification technology was developed. This waste aged in the steel tanks and reacted with the NaOH, resulting in stratification into a sludge, salt cake, and salt solution. The sludge consists primarily of precipitates of hydroxides of iron and aluminum, and may vary from a high aluminum containing waste (HM) to a high iron containing waste (Purex). This sludge contains most of the radioactivity in the waste except for radioactive cesium. The salt cake and salt solution contain mainly sodium salts of common anions (nitrate, nitrite, aluminate, and hydroxide). The salt fraction contains most of the radioactive cesium and only trace amounts of other radioactive species.

The sludge is washed in waste storage tanks (1) in order to remove as much of the soluble nonradioactive ingredients as possible. Cesium is removed from the soluble salt fraction of the waste by precipitation as cesium tetraphenylborate. Residual strontium and plutonium in the salt waste are adsorbed on a small amount of sodium titanate. The resulting decontaminated salt waste is mixed with cement and disposed of as large monoliths. The resulting washed slurries are concentrated and pumped to the DWPF (2).

Formic acid hydrolysis (3) is used to separate a precipitate hydrolysis aqueous product (PHA) (4), which contains glass forming sodium and boron, from the organic decomposition products of the tetraphenylborate salt in the salt-processing cell. Organic decomposition products are incinerated (5), and the PHA is transferred to the slurry receipt adjustment tank (6), where it is blended with washed sludge slurry. Any mercury in the waste is reduced to metallic form by the formic acid, and removed by steam stripping (7). Nitric acid (8) is also added to prevent glass redox problems. The purified sludge-PHA mixture (9) is sent to a slurry mix evaporator (SME) (10), where a glass frit (11) is added. Any chemical adjustment of the glass formulation must be made in the SME. Multiple SME batches are stored in the melter feed tank (MFT) (12) before slurry feeding to the DWPF melter (13).

After vitrification at 1150° C., the glass is poured from the melter into stainless steel canisters (14) by a differential pressure technique. After filling, temporary seals are inserted into the canisters to prevent the introduction of water during decontamination. Contamination is removed from the canister surface by air-injected frit blasting (15). After decontamination, the canister is sealed using an upset resistance welding technique (16). The cleaned and sealed canisters are then sent to an interim storage facility (17) where they remain until shipment to a repository. The spent frit used to decontaminate the canisters is recycled to the melter via the SME.

Because chemical adjustment of the glass formulation must be done in the SME, and because durability testing of the product and analysis of the leachate requires at least one week to complete, it is necessary to relate glass durability to parameters that are easily measured before the feed is sent to the melter, i.e., the composition of the feedstock glass-forming materials, such as the glass frit, the washed sludge, and the PHA.

The method of determining glass durability based upon the composition of the feedstock materials according to the present invention allows the feedstock materials to be altered prior to feeding to the melter, in order to maximize waste loading of the resulting glass, minimize the use of purchased frit, and achieve acceptable durability without the need for measuring melt or glass properties in situ, and without the need first to prepare a sample of glass to be evaluated, since unacceptable waste glass, once made, cannot be remedied or reworked, and since the time and expense involved in reworking other glasses can be avoided.

An illustrative, nonlimiting example of the process according to the present invention as applied to the DWPF is given below:

EXAMPLE

A glass composition to be formed in the DWPF is expected to have the following composition, in percent by weight, based upon the glass forming feedstock materials (glass frit, PHA, washed sludge): $Na_2O$ 23.55; FeO 3.28; $B_2O_3$ 5.25; CaO 4.26; $SiO_2$ 62.00. The mole fraction of each oxide species is calculated as follows:

Calculation of the Mole Fraction of Oxide Species (Moles of Glass Oxides/Gram of Glass)

| Glass Composition Oxide Species | Oxide Wt % | Molecular Wt. of Oxide Species | $f_i = \frac{\text{mol oxide}}{100 \text{ g glass}}$ |
|---|---|---|---|
| $Na_2O$ | 23.55 | 61.98 | 0.3800 |
| FeO | 3.28 | 71.85 | 0.0456 |
| $B_2O_3$ | 5.25 | 69.62 | 0.0754 |
| CaO | 4.26 | 56.08 | 0.0760 |
| $SiO_2$ | 62.00 | 60.08 | 1.0320 |
| | 98.34 | | 1.6090 |

Next, mole fractions of associated complexes and nonassociated reactant species are calculated as follows:

Calculation of the Mole Fraction of Associated and Non-Associated Glass Reactant Species from the Glass Composition

| Glass Composition Oxide Species | $f_i = \frac{\text{mol oxide}}{100 \text{ g glass}}$ | Structurally Associated Glass Components Glass Reagents | $f_i = \frac{\text{mol oxide}}{100 \text{ g glass}}$ |
|---|---|---|---|
| $Na_2O$ | 0.3800 | $\{Na_2O + SiO_2\}$ | 0.3800 |
| FeO | 0.0456 | $\{FeO + SiO_2\}$ | 0.0456 |
| $B_2O_3$ | 0.0754 | $B_2O_3$ | 0.0754 |
| CaO | 0.0760 | $\{CaO + SiO_2\}$ | 0.0760 |
| $SiO_2$ | 1.0320 | $SiO_2$ | 0.5304 |
| SUM | 1.6090 | | 1.1074 |

The silica included in each associated complex depletes the available moles of unassociated silica by the number of moles assigned to the associated complex.

A preliminary glass dissolution estimator, $\Delta G_p$, is calculated by weighting the partial molar hydration free energy values for each hydration reaction and summing these weighted values, as follows:

Calculation of the Preliminary Free Energy of Hydration, $\Delta G_p$

| Structurally Associated Silicate and Oxide Species | $f_i = \frac{\text{mol oxide}}{100 \text{ g glass}}$ | $\Delta G_i$ (kcal/mole) (from Table IX) | $\Sigma(\Delta G_i \cdot f_i)$ (kcal/100 g glass) |
|---|---|---|---|
| $\{Na_2O + SiO_2\}$ | 0.3800 | −49.04 | −18.64 |
| $\{FeO + SiO_2\}$ | 0.0456 | −17.28 | −0.79 |
| $\{B_2O_3\}$ | 0.0754 | −10.43 | −0.79 |
| $\{CaO + SiO_2\}$ | 0.0760 | −9.74 | −0.74 |
| $SiO_2$ | 0.5304 | +4.05 | +2.148 |
| SUM | 1.1074 | $\Delta G_p =$ | −18.81 (kcal/100 g) |

An accelerated glass dissolution function, $\Delta G_a$, is determined by first determining the expected pH of the aqueous glass solution as follows:

$$pH_{det} = -3.81[Al_2O_3] - 2.82[B_2O_3] -$$

$$219.88[BaO] + 215.82[CuO] + 2.74[FeO] - 5.36[K_2O] +$$

$$6.74[Li_2O] + 6.30[MnO] + 12.74[Na_2O] + 113.12[SrO] +$$

$$25.42[TiO_2] - 25.67[ZnO] + 7.58 = 12.25$$

The contribution of weak acid dissociation at the determined pH, $\Delta G_a^{WA}$, is then determined as follows:

$$\Delta G_a^{WA} = -1.364 \left\{ \log \left[ 1 + \frac{10^{-10}}{10^{-(12.25)}} + \frac{10^{-21.994}}{10^{-2(12.25)}} \right] + \log \left[ 1 + \frac{10^{-9.18}}{10^{-(12.25)}} + \frac{10^{-21.89}}{10^{-2(12.25)}} + \frac{10^{-35.69}}{10^{-3(12.25)}} \right] \right\}$$

$$= -8.042 (kcal/\text{mol glass})$$

The units of this contribution are adjusted (i.e., the contribution is "denormalized") as follows:

$$\left( \frac{100}{MW} \right) \Delta G_a^{WA} = (1.609)(-8.042) = -12.94 (kcal/100g \text{ glass})$$

The relevant pH dependent partial molar hydration free energies for the reactant species present and for the determined pH are selected from Table V above, and the weighted contribution from each reactant is determined and summed to determine $\Delta G_a^{SB}$ as follows:

Calculation of the Amount of Accelerated Matrix Attack to the $\Delta G_a$ for each Silicate Glass Reactant in predicted pH regimes >11

| Glass Reactants | $f_i = \frac{\text{mol oxide}}{100 \text{ g glass}}$ | $\Delta G_i$ (kcal/mole) | $\Sigma(\Delta G_i \cdot f_i)$ (kcal/100 g glass) |
|---|---|---|---|
| {Na$_2$O + SiO$_2$} | 0.3800 | | |
| {FeO + SiO$_2$} | 0.0456 | | |
| B$_2$O$_3$ | 0.0754 | −23.37 | −1.76 |
| {CaO + SiO$_2$} | 0.0760 | | |
| SiO$_2$ | 0.4550 | −1.5 | −0.68 |
| | 1.0320 | $\Delta G_a^{SB}$ = | −2.44 kcal/100 g glass |

Calculation of the Amount of Accelerated Matrix Attack to the $\Delta G_a^{SB}$ for each Silicate Glass Reactant in predicted pH regimes >12

| Structurally Associated Silicate and Oxide Species | $f_i = \frac{\text{mol oxide}}{100 \text{ g glass}}$ | $\Delta G_i$ (kcal/mole) | $\Sigma(\Delta G_i \cdot f_i)$ (kcal/100 g glass) |
|---|---|---|---|
| {Na$_2$O + SiO$_2$} | 0.3800 | | |
| {FeO + SiO$_2$} | 0.0456 | | |
| B$_2$O$_3$ | 0.0754 | −24.29 | −1.83 |
| {CaO + SiO$_2$} | 0.0760 | | |
| SiO$_2$ | 0.4550 | −2.82 | −1.28 |
| | 1.0320 | $\Delta G_a^{SB}$ = | −3.11 (kcal/100 g glass) |

$$\Delta G_a = \left( \frac{100}{MW} \right) \Delta G_a^{WA} + \Delta G_a^{SB>11} + \Delta G_a^{SB>12} = -12.94 - 2.44 - 3.11 = -3.11 = -18.49 (kcal/100g \text{ glass})$$

Note that other stable hydration products occur in the pH regimes >12 for elements such as Ru, Te, Mn, P, Pb and Sn. However, the effects of these pH-dependent $\Delta G_i$ are not considered in this example since DWPF glass contains trace quantities of these species.

The final free energy of hydration, $\Delta G_f$, is then determined as follows:

$$\Delta G_f = -18.80 - 18.49 = -37.29 (kcal/100g \text{ glass})$$

This final free energy of hydration is then used to determine normalized concentrations of B, Li, and Na in the leachate, using the correlation equations discussed above. These concentrations are then compared to the mean allowable concentration obtained by subjecting a benchmark waste glass identified in the DWPF Environmental Assessment to the Product Consistency Test (PCT, ASTM C1285-94). In addition, a frit component function and a sludge component function are determined using the formulae disclosed above, and tested against the phase separation discriminator inequality disclosed above. If the concentrations determined above are more than two standard deviations below the mean of the benchmark glass, and the phase separation discriminator inequality is satisfied, the glass forming feedstocks are forwarded to the melter. If the concentrations determined above are less than two standard deviations below the mean, or the phase separation inequality is not satisfied, then one or more of the feedstock streams is subjected to remediation. For instance, more sludge or more Al$_2$O$_3$ could be added to drive the composition from phase separation to homogeneity, or the composition or amount of the glass forming flit could be adjusted to obtain a more durable composition.

A number of glasses were prepared using the SRS DWPF process, discussed above, on simulated waste feedstocks. During these runs, A series of "Functional Acceptance" runs of glass (the FA series) were used to build the melter inventory to an acceptable operating level and to achieve stable melter operation. The glass forming frit used to make the glasses for the FA series was specifically designed for reactor startup, as described in Jantzen, "Characterization of Defense Waste Processing Facility (DWPF) Startup Frit," U.S. DOE Report WSRC-RP-89-18, Westinghouse Savannah River Co., Savannah River Laboratory, Aiken, S.C. (1989). The last of the FA series was designated FA-13, and used a feedstock of blend sludge, PHA, and frit 202 (described in Schumacher, "Errors of DWPF Frit Analysis—Final Report," U.S. DOE Report WSRC-RP-92-37, Westinghouse Savannah River Co., Savannah River Technology Center, Aiken, S.C. (January, 1992). The blend sludge feedstock had a composition representing variations about the composite feed expected to the DWPF.

During Waste Qualification Runs, the simulated waste fed to DWPF went through large, abrupt changes in composition, for two reasons. First, simulated waste feedstocks were used to represent the extremes in waste composition that will be fed to the melter, since chemical composition is the most important factor in determining the leaching behavior of glass in water. In addition, it was desired to assess the use of the method of the present invention to control the DWPF during times of rapidly changing feed composition. The first qualification run, WP-14, used the same feedstocks as the FA-13 run, except that the composite sludge was doped with Nd as a melt tracer, in order to show that the melter behaved as a continuous stirred tank reactor. The second qualification run, WP-15, was intended to provide a rapid transition between the composite sludge and a sludge having a high Fe concentration, and thus low resultant viscosity. The third run, WP-16, represented an extreme change in simulated sludge composition including a high Al concentration (and correspondingly high melt viscosity). The final qualification run, WP-17, used a composite sludge feed representing an abrupt return to normal melter operation from a condition of high melt viscosity.

The pH of the expected leachate solution was determined, and the $\Delta G_p$, $$\Delta G_p, \frac{100}{MW} \Delta G_a^{WA},$$

Figure 3:
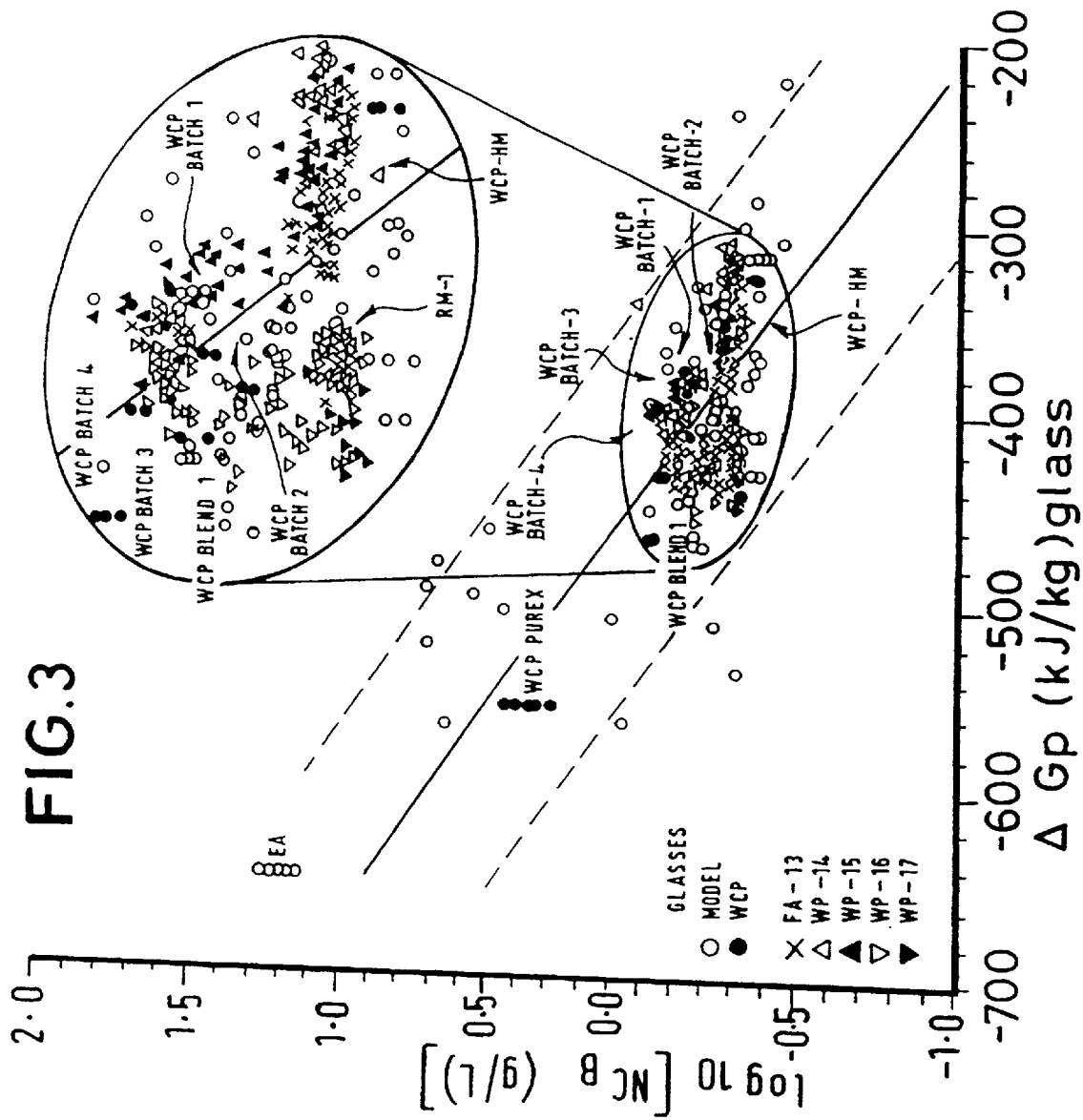
FIG. 3 is a diagram showing the relationship between the leaching response of boron and $\Delta G_f$ determined according to the invention, and the actual leaching behavior of glasses produced.
Figure 4:
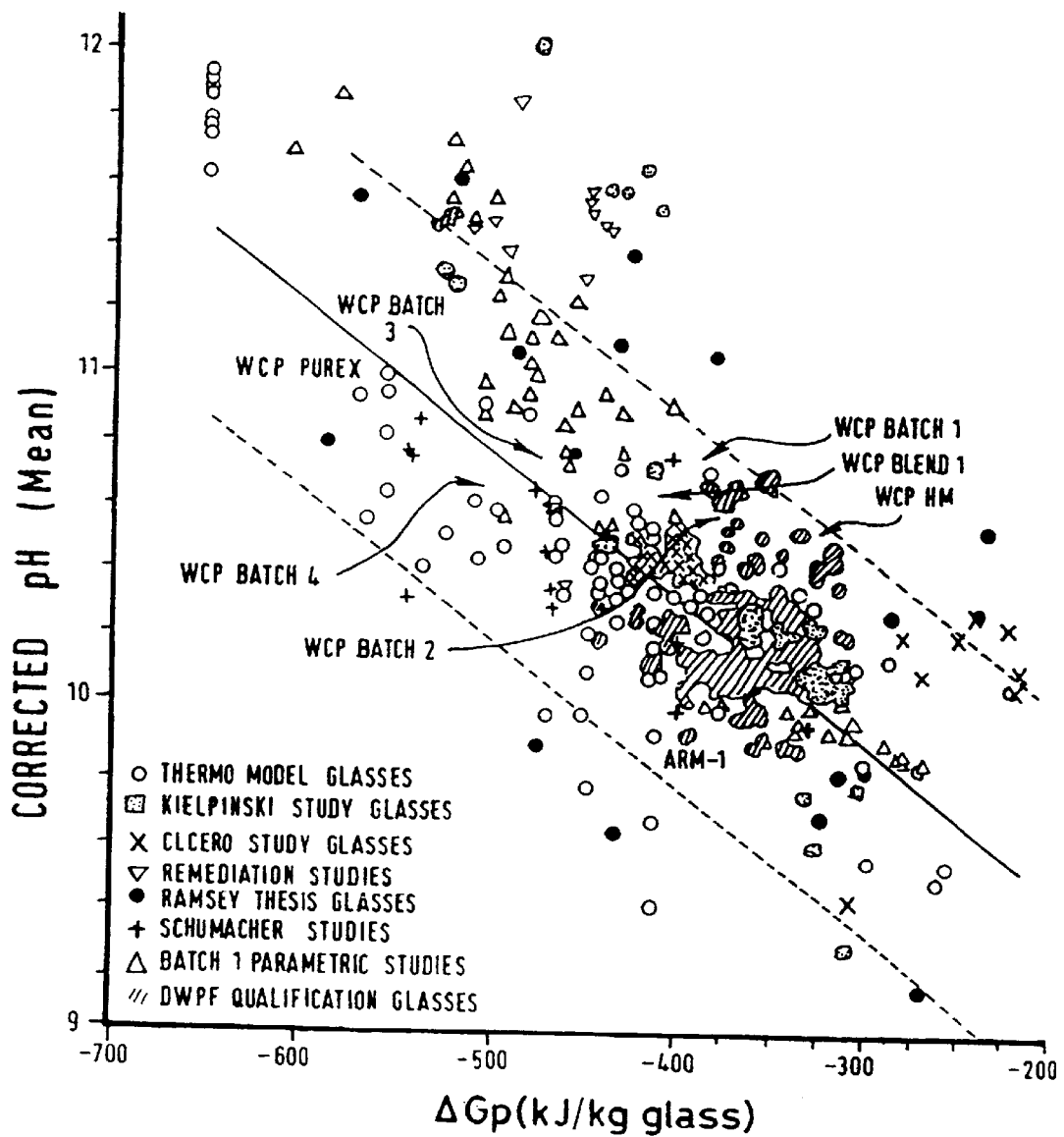
FIG. 4 is a diagram showing the relationship between measured and bias corrected pH and $\Delta G_p$ for boron.

, and $\Delta G_f$ parameters were determined using the methods described above, and values for $\log_{10}[NC_i(g/L)]$ were determined according to the present invention, as described above. The predicted values for $\log_{10}[NC_B(g/L)]$ are shown in FIG. 3 as a straight line. Overlain on these values are the actual measured leaching results for the FA-13 and WP-14 to WP-17 campaigns, as well as the measurements of actual glasses used to obtain the straight line relation between $\Delta G_f$ and $\log_{10}[NC_B(g/L)]$ (i.e., the "Model Data"). Each $\log_{10}$ $[NC_B(g/L)]$ point is the average of three durability test responses. Over 387 glass samples were analyzed and plotted. Confidence limits (95%) for the individual glasses are represented by two straight lines parallel to the predicted leachate response. The actual leachate response for the FA-13 and WP-14 to WP-17 glasses are provided in the Table VI, below. The actual leaching data obtained for these simulated waste glasses agreed very well with the leaching behaviour determined according to the present invention, despite wide variations in sludge feed and glass fluidity. Similar figures can be constructed for Si, Li, and Na based upon the data in Table VI.

TABLE VI pH, Free Energies of Hydration ($\Delta G_p$, $\Delta G_a$, and $\Delta G_f$), and PCT (ASTM C1285-94) Normalized Release Rates for DWPF "Model Validation Data"

| | | kcal/100 g glass | | | $\log_{10}[NC_i(g/L)]$ | | | |
|---|---|---|---|---|---|---|---|---|
| Sample | pH | $\Delta G_p$ | $\frac{100}{MW}\Delta G_a^{WA}$ | $\Delta G_f$ | B | Li | Na | Si |
| FA-13:GRAB-S00004 | 9.96 | −8.428 | −4.386 | −12.814 | −0.2532 | −0.2013 | −0.2422 | −0.4518 |
| FA-13:GRAB-S00010 | 10.43 | −8.963 | −4.633 | −13.596 | −0.2596 | −0.207 | −0.2567 | −0.4353 |
| FA-13:GRAB-S00111 | 10.27 | −8.888 | −4.416 | −13.304 | −0.2451 | −0.2078 | −0.247 | −0.4218 |
| FA-13:GRAB-S00112 | 10.04 | −8.567 | −4.293 | −12.861 | −0.264 | −0.1888 | −0.1547 | −0.4108 |
| FA-13:GRAB-S00114 | 9.95 | −8.733 | −4.366 | −13.098 | −0.2443 | −0.1907 | −0.2435 | −0.4248 |
| FA-13:GRAB-S00122 | 10.04 | −8.951 | −4.313 | −13.264 | −0.2399 | −0.2093 | −0.2137 | −0.423 |
| FA-13:GRAB-S00123 | 10.42 | −8.652 | −4.304 | −12.956 | −0.2649 | −0.2084 | −0.2533 | −0.439 |
| FA-13:GRAB-S00145 | 10.42 | −8.502 | −4.272 | −12.774 | −0.2466 | −0.1936 | −0.2322 | −0.4329 |
| FA-13:GRAB-S00146 | 9.9 | −9.351 | −5.115 | −14.466 | −0.2335 | −0.1839 | −0.2563 | −0.4219 |
| FA-13:GRAB-X00101 | 9.98 | −8.555 | −4.289 | −12.844 | −0.2536 | −0.1948 | −0.2499 | −0.4337 |
| FA-13:SECT-S00004-24.875H-5R | 10.07 | −8.777 | −4.428 | −13.205 | −0.2602 | −0.2263 | −0.2718 | −0.4578 |
| FA-13:SECT-S00004-25.25H-3.75R | 10.3 | −8.671 | −4.417 | −13.089 | −0.2648 | −0.2161 | −0.2649 | −0.4413 |
| FA-13:SECT-S00004-25.4H-4R | 10.27 | −8.701 | −4.406 | −13.107 | −0.2698 | −0.2218 | −0.2729 | −0.4459 |
| FA-13:SECT-S00004-25.5H-14.5R | 10.21 | −8.705 | −4.377 | −13.081 | −0.2735 | −0.2241 | −0.2732 | −0.4481 |
| FA-13:SECT-S00004-25.75H-3.5R | 10.22 | −8.816 | −4.484 | −13.299 | −0.2705 | −0.2228 | −0.2695 | −0.4481 |
| FA-13:SECT-S00004-53.156H-4R | 10.25 | −8.616 | −4.371 | −12.987 | −0.2816 | −0.2364 | −0.2702 | −0.4611 |
| FA-13:SECT-S00004-53.356H-5.5R | 10.26 | −8.488 | −4.225 | −12.714 | −0.2837 | −0.238 | −0.2732 | −0.4634 |
| FA-13:SECT-S00004-53.41H-10.5R | 10.24 | −8.522 | −4.22 | −12.742 | −0.2793 | −0.2264 | −0.2657 | −0.4535 |
| FA-13:SECT-S00004-53.78H-3.25R | 10.15 | −8.694 | −4.417 | −13.11 | −0.2677 | −0.2213 | −0.2644 | −0.45 |
| FA-13:SECT-S00004-82.31H-12.5R | 9.86 | −8.526 | −4.322 | −12.848 | −0.2918 | −0.2411 | −0.2854 | −0.4726 |
| FA-13:SECT-S00004-82.31H-4R | 9.95 | −8.59 | −4.362 | −12.951 | −0.2977 | −0.2541 | −0.2846 | −0.4771 |
| FA-13:SECT-S00004-82.56H-1R | 9.99 | −8.503 | −4.343 | −12.846 | −0.2725 | −0.2245 | −0.2653 | −0.4525 |
| FA-13:SECT-S00004-82.56H-3R | 9.88 | −8.403 | −4.253 | −12.656 | −0.2734 | −0.2258 | −0.2614 | −0.4556 |
| FA-13:SECT-S00114-25.78H-11R | 10.53 | −8.854 | −4.473 | −13.327 | −0.2775 | −0.2293 | −0.2844 | −0.449 |
| FA-13:SECT-S00114-25.91H-2.13R | 10.6 | −9.073 | −4.74 | −13.813 | −0.2903 | −0.2455 | −0.297 | −0.456 |
| FA-13:SECT-S00114-25.91H-3.75R | 10.47 | −8.886 | −4.531 | −13.417 | −0.2793 | −0.2418 | −0.2865 | −0.4556 |
| FA-13:SECT-S00114-25.91H-3R | 10.67 | −9.14 | −4.759 | −13.898 | −0.2734 | −0.2308 | −0.2873 | −0.4478 |
| FA-13:SECT-S00114-26.66H-4R | 10.55 | −8.752 | −4.459 | −13.211 | −0.2343 | −0.2067 | −0.2521 | −0.4475 |
| FA-13:SECT-S00114-52.66H-12R | 10.75 | −8.503 | −4.202 | −12.705 | −0.2822 | −0.2371 | −0.2648 | −0.4532 |
| FA-13:SECT-S00114-53.41H-9R | 10.7 | −8.331 | −4.136 | −12.467 | −0.2943 | −0.2437 | −0.2684 | −0.4659 |
| FA-13:SECT-S00114-54.91H-1.5R | 10.69 | −8.415 | −4.213 | −12.628 | −0.2903 | −0.2434 | −0.2693 | −0.4606 |
| FA-13:SECT-S00114-54.91H-3.5R | 10.68 | −8.427 | −4.2 | −12.627 | −0.2978 | −0.2501 | −0.274 | −0.467 |
| FA-13:SECT-S00114-75.91H-6.5R | 10.66 | −9.086 | −4.722 | −13.808 | −0.284 | −0.2366 | −0.2983 | −0.4599 |
| FA-13:SECT-S00114-76.91H-12R | 10.66 | −8.765 | −4.46 | −13.225 | −0.2774 | −0.2399 | −0.2939 | −0.4676 |
| FA-13:SECT-S00114-77.91H-3R | 10.62 | −8.819 | −4.46 | −13.279 | −0.2884 | −0.2338 | −0.2876 | −0.4592 |
| FA-13:SECT-S00114-76.91H-4R | 10.58 | −8.564 | −4.227 | −12.791 | −0.2963 | −0.2445 | −0.2843 | −0.4622 |
| FA-13:SECT-S00146-25.1875H-12R | 10.08 | −8.622 | −4.244 | −12.866 | −0.2785 | −0.2285 | −0.2785 | −0.4466 |
| FA-13:SECT-S00146-25.1875H-6.5R | 10.1 | −8.58 | −4.28 | −12.86 | −0.2842 | −0.2325 | −0.2737 | −0.4483 |
| FA-13:SECT-S00146-25.56H-3R | 10.23 | −8.899 | −4.299 | −13.197 | −0.2655 | −0.2089 | −0.2642 | −0.4114 |
| FA-13:SECT-S00146-25.94H-1.5R | 10.07 | −8.633 | −4.345 | −12.978 | −0.2847 | −0.2287 | −0.272 | −0.443 |
| FA-13:SECT-S00146-52.06H-12R | 10.19 | −8.587 | −4.335 | −12.922 | −0.2879 | −0.2337 | −0.2675 | −0.4438 |
| FA-13:SECT-S00146-52.94H-4.125R | 10.24 | −8.446 | −4.586 | −13.032 | −0.2904 | −0.2354 | −0.2616 | −0.4451 |
| FA-13:SECT-S00146-52.94H-4R | 10.21 | −8.516 | −4.249 | −12.764 | −0.2833 | −0.2344 | −0.2729 | −0.4499 |
| FA-13:SECT-S00146-53.31H-1.875R | 10.2 | −8.633 | −4.373 | −13.006 | −0.2824 | −0.2294 | −0.2769 | −0.4438 |
| FA-13:SECT-S00146-81.06H-9R | 10.09 | −8.707 | −4.271 | −12.977 | −0.2787 | −0.2234 | −0.267 | −0.4396 |
| FA-13:SECT-S00146-81.81H-3.375R | 10.2 | −9.159 | −4.812 | −13.971 | −0.2822 | −0.2295 | −0.2807 | −0.4426 |
| FA-13:SECT-S00146-81.94H-4.75R | 10.13 | −9.182 | −5.005 | −14.187 | −0.2892 | −0.2311 | −0.2926 | −0.4513 |
| FA-13:SECT-S00146-82.06H-3.75R | 10.32 | −8.772 | −4.452 | −13.224 | −0.2819 | −0.2303 | −0.2659 | −0.4453 |
| FA-13:SECT-S00146-82.31H-9.5R | 10.18 | −8.697 | −4.544 | −13.241 | −0.2862 | −0.2314 | −0.2793 | −0.4515 |
| FA-13:WALL-S00112-77.5H-1.5R | 10.44 | −8.527 | −4.221 | −12.748 | −0.2862 | −0.2341 | −0.2651 | −0.4486 |
| FA-13:WALL-S00123-61H-2.25R | 10.12 | −8.573 | −4.256 | −12.828 | −0.2653 | −0.2188 | −0.246 | −0.4377 |
| FA-13:WALL-S00145-25.25H-2R | 10.5 | −8.419 | −4.204 | −12.623 | −0.2718 | −0.2258 | −0.2501 | −0.4464 |
| WP-14:GRAB-S00001 | 10.22 | −8.111 | −3.744 | −11.855 | −0.2924 | −0.2243 | −0.2757 | −0.4753 |
| WP-14:GRAB-S00002 | 10.2 | −7.922 | −3.577 | −11.499 | −0.2676 | −0.2147 | −0.2596 | −0.4591 |

TABLE VI-continued pH, Free Energies of Hydration ($\Delta G_p$, $\Delta G_a$, and $\Delta G_f$), and PCT (ASTM C1285-94) Normalized Release Rates for DWPF "Model Validation Data"

| | | kcal/100 g glass | | | $\log_{10}$ [NC$_i$(g/L)] | | | |
|---|---|---|---|---|---|---|---|---|
| Sample | pH | $\Delta G_p$ | $\frac{100}{MW}\Delta G_a^{WA}$ | $\Delta G_f$ | B | Li | Na | Si |
| WP-14:GRAB-S00006 | 10.19 | −8.018 | −3.787 | −11.806 | −0.2924 | −0.2195 | −0.284 | −0.4747 |
| WP-14:GRAB-S00009 | 10.24 | −7.796 | −3.649 | −11.446 | −0.3069 | −0.2416 | −0.2896 | −0.4937 |
| WP-14:GRAB-S00155 | 10.22 | −7.715 | −3.452 | −11.167 | −0.2649 | −0.21 | −0.2518 | −0.4526 |
| WP-14:GRAB-S00402 | 10.2 | −7.752 | −3.577 | −11.329 | −0.2758 | −0.21 | −0.2366 | −0.4798 |
| WP-14:SECT-S00001-31.38H-6.5R | 10.51 | −7.952 | −3.634 | −11.586 | −0.2758 | −0.2244 | −0.273 | −0.4635 |
| WP-14:SECT-S00001-31.88H-11.5R | 10.29 | −7.985 | −3.693 | −11.678 | −0.2731 | −0.2268 | −0.2731 | −0.4647 |
| WP-14:SECT-S00001-32.38H-5.5R | 10.26 | −8.029 | −3.733 | −11.762 | −0.3012 | −0.2546 | −0.2812 | −0.4788 |
| WP-14:SECT-S00001-32.63H-1.0R | 10.21 | −7.907 | −3.59 | −11.497 | −0.265 | −0.2124 | −0.2623 | −0.4597 |
| WP-14:SECT-S00001-65.63H-8.5R | 10.45 | −8.164 | −3.754 | −11.918 | 0.0372 | −0.0412 | −0.0848 | −0.4592 |
| WP-14:SECT-S00001-66.13H-11.5R | 9.87 | −8.125 | −3.84 | −11.965 | −0.284 | −0.2341 | −0.273 | −0.4696 |
| WP-14:SECT-S00001-66.88H-2.5R | 10.19 | −7.369 | −3.175 | −10.544 | −0.2777 | −0.2341 | −0.2366 | −0.4609 |
| WP-14:SECT-S00001-67.13H-5.0R | 9.86 | −7.96 | −3.666 | −11.626 | −0.2703 | −0.2316 | −0.257 | −0.4617 |
| WP-14:SECT-S00001-67.38H-4.0R | 10.19 | −7.851 | −3.615 | −11.466 | −0.2623 | −0.2148 | −0.2654 | −0.4581 |
| WP-14:SECT-S00001-82.75H-6.0R | 10.15 | −8.266 | −4.02 | −12.286 | −0.2703 | −0.2218 | −0.273 | −0.4629 |
| WP-14:SECT-S00001-84.75H-11.0R | 10.15 | −8.113 | −3.893 | −12.005 | −0.2676 | −0.2123 | −0.273 | −0.4634 |
| WP-14:SECT-S00001-85.25H-1.25R | 10.19 | −8.09 | −3.858 | −11.947 | −0.2982 | −0.2416 | −0.2953 | −0.4739 |
| WP-14:SECT-S00001-85.75H-5.0R | 10.14 | −8.328 | −4.084 | −12.412 | −0.3386 | −0.2916 | −0.3483 | −0.5311 |
| WP-14:SECT-S00002-12.88H-1.5R | 10.09 | −7.834 | −3.727 | −11.561 | −0.2984 | −0.2547 | −0.2928 | −0.4906 |
| WP-14:SECT-S00002-13.13H-8.0R | 10.08 | −7.769 | −3.72 | −11.488 | −0.2812 | −0.2341 | −0.2785 | −0.4739 |
| WP-14:SECT-S00002-13.38H-11.5R | 10.07 | −7.86 | −3.787 | −11.647 | −0.2785 | −0.2341 | −0.2812 | −0.4809 |
| WP-14:SECT-S00002-13.38H-5.0R | 10.11 | −7.86 | −3.78 | −11.64 | −0.3099 | −0.2571 | −0.3069 | −0.4969 |
| WP-14:SECT-S00002-57.94H-11.5R | 10.08 | −7.968 | −3.659 | −11.626 | −0.2982 | −0.2518 | −0.2924 | −0.4716 |
| WP-14:SECT-S00002-57.94H-3.5R | 10.06 | −7.782 | −3.501 | −11.284 | −0.2812 | −0.2492 | −0.2841 | −0.4693 |
| WP-14:SECT-S00002-58.44H-5.5R | 10.08 | −8.16 | −3.789 | −11.948 | −0.273 | −0.2316 | −0.2841 | −0.4582 |
| WP-14:SECT-S00002-58.94H-3.0R | 10.05 | −7.858 | −3.593 | −11.451 | −0.2982 | −0.2623 | −0.2953 | −0.4788 |
| WP-14:SECT-S00002-87.13H-11.5R | 10.08 | −7.796 | −3.598 | −11.395 | −0.3099 | −0.2492 | −0.3011 | −0.4837 |
| WP-14:SECT-S00002-87.88H-4.0R | 10.09 | −7.714 | −3.559 | −11.273 | −0.284 | −0.2291 | −0.284 | −0.4715 |
| WP-14:SECT-S00002-88.13H-5.5R | 10.07 | −7.659 | −3.468 | −11.127 | −0.284 | −0.2243 | −0.284 | −0.4713 |
| WP-14:SECT-S00002-88.63H-1.5R | 10.06 | −7.917 | −3.746 | −11.663 | −0.2786 | −0.2268 | −0.2813 | −0.4729 |
| WP-14:SECT-S00006-20.25H-6.75R | 10.08 | −7.646 | −3.564 | −11.21 | −0.2982 | −0.2443 | −0.2789 | −0.4899 |
| WP-14:SECT-S00006-20.75H-2.5R | 10.1 | −7.73 | −3.626 | −11.356 | −0.2896 | −0.2342 | −0.2813 | −0.4738 |
| WP-14:SECT-S00006-21.0H-4.0R | 10.1 | −7.462 | −3.452 | −10.914 | −0.3012 | −0.2545 | −0.2842 | −0.4946 |
| WP-14:SECT-S00006-22.13H-11.5R | 10.21 | −7.43 | −3.407 | −10.837 | −0.2757 | −0.2147 | −0.2492 | −0.4723 |
| WP-14:SECT-S00006-44.56H-3.0R | 10.22 | −7.915 | −3.644 | −11.559 | −0.1916 | −0.1783 | −0.2366 | −0.4729 |
| WP-14:SECT-S00006-45.06H-3.0R | 10.15 | −7.879 | −3.603 | −11.482 | −0.2896 | −0.2243 | −0.2812 | −0.4669 |
| WP-14:SECT-S00006-45.06H-4.0R | 10.2 | −7.887 | −3.626 | −11.513 | −0.273 | −0.2171 | −0.2649 | −0.4627 |
| WP-14:SECT-S00006-45.56H-10.5R | 10.19 | −8.257 | −3.918 | −12.176 | −0.2757 | −0.2147 | −0.2812 | −0.4598 |
| WP-14:SECT-S00006-45.56H-4.0R | 10.17 | −7.941 | −3.683 | −11.623 | −0.2896 | −0.2341 | −0.2896 | −0.4706 |
| WP-14:SECT-S00006-75.12H-12.0R | 10.22 | −7.706 | −3.337 | −11.043 | −0.2757 | −0.2243 | −0.2649 | −0.4669 |
| WP-14:SECT-S00006-75.62H-4.0R | 10.19 | −7.879 | −3.529 | −11.408 | −0.2812 | −0.2316 | −0.2703 | −0.4634 |
| WP-14:SECT-S00006-76.62H-1.5R | 10.2 | −7.827 | −3.506 | −11.333 | −0.273 | −0.2195 | −0.257 | −0.459 |
| WP-14:SECT-S00006-77.12H-5.5R | 10.15 | −7.847 | −3.446 | −11.293 | −0.273 | −0.2219 | −0.257 | −0.4579 |
| WP-14:SECT-S00009-23.08H-6.0R | 10.2 | −8.239 | −3.925 | −12.164 | −0.304 | −0.2544 | −0.3128 | −0.4911 |
| WP-14:SECT-S00009-23.58H-10.5R | 10.23 | −8.098 | −3.734 | −11.832 | −0.2924 | −0.2441 | −0.2982 | −0.4825 |
| WP-14:SECT-S00009-23.83H-3.5R | 10.22 | −8.069 | −3.792 | −11.861 | −0.301 | −0.2544 | −0.3158 | −0.4979 |
| WP-14:SECT-S00009-23.83H-4.75R | 10.24 | −8.199 | −3.843 | −12.042 | −0.2982 | −0.257 | −0.3158 | −0.4854 |
| WP-14:SECT-S00009-24.08H-2.0R | 10.24 | −8.082 | −3.794 | −11.875 | −0.3128 | −0.2597 | −0.2953 | −0.4909 |
| WP-14:SECT-S00009-24.08H-6.13R | 10.25 | −8.123 | −3.806 | −11.929 | −0.2841 | −0.2366 | −0.2841 | −0.4777 |
| WP-14:SECT-S00009-50.71H-4.0R | 10.23 | −7.899 | −3.447 | −11.347 | −0.2785 | −0.2416 | −0.2785 | −0.4671 |
| WP-14:SECT-S00009-50.96H-5.0R | 10.23 | −7.882 | −3.403 | −11.284 | −0.2812 | −0.2341 | −0.2703 | −0.4714 |
| WP-14:SECT-S00009-51.21H-6.0R | 10.18 | −7.821 | −3.426 | −11.248 | −0.2785 | −0.2367 | −0.2704 | −0.4715 |
| WP-14:SECT-S00009-51.46H-10.0R | 10.2 | −7.667 | −3.285 | −10.952 | −0.2953 | −0.2518 | −0.2896 | −0.4881 |
| WP-14:SECT-S00009-70.27H-11.0R | 10.21 | −7.683 | −3.489 | −11.172 | −0.2703 | −0.21 | −0.2518 | −0.4638 |
| WP-14:SECT-S00009-70.52H-6.5R | 10.19 | −7.743 | −3.582 | −11.325 | −0.2757 | −0.2147 | −0.2596 | −0.4712 |
| WP-14:SECT-S00009-72.02H-2.0R | 10.18 | −7.959 | −3.799 | −11.758 | −0.2785 | −0.2292 | −0.2785 | −0.4761 |
| WP-14:SECT-S00009-72.02H-3.0R | 10.12 | −7.766 | −3.539 | −11.304 | −0.2896 | −0.2267 | −0.273 | −0.4772 |
| WP-14:SECT-S00155-20.0H-4.0R | 10.02 | −7.766 | −3.509 | −11.275 | −0.3158 | −0.265 | −0.3069 | −0.4885 |
| WP-14:SECT-S00155-20.0H-8.5R | 10.1 | −7.873 | −3.596 | −11.468 | −0.2897 | −0.2366 | −0.2868 | −0.4715 |
| WP-14:SECT-S00155-23.0H-11.0R | 10.07 | −7.702 | −3.45 | −11.152 | −0.3069 | −0.2623 | −0.2982 | −0.4774 |
| WP-14:SECT-S00155-23.0H-3.5R | 10.02 | −7.687 | −3.435 | −11.121 | −0.2868 | −0.2316 | −0.2757 | −0.4744 |
| WP-14:SECT-S00155-53.25H-10.0R | 10.07 | −8.15 | −3.737 | −11.887 | −0.3069 | −0.257 | −0.3128 | −0.4846 |
| WP-14:SECT-S00155-54.75H-2.0R | 10.03 | −7.873 | −3.54 | −11.413 | −0.2758 | −0.2417 | −0.2813 | −0.4649 |
| WP-14:SECT-S00155-55.0H-2.75R | 10.09 | −7.931 | −3.537 | −11.468 | −0.2596 | −0.2218 | −0.2676 | −0.4501 |
| WP-14:SECT-S00155-55.25H-2.0R | 10.06 | −7.987 | −3.598 | −11.585 | −0.2925 | −0.2519 | −0.2953 | −0.483 |
| WP-14:SECT-S00155-80.69H-11.0R | 10.09 | −7.781 | −3.517 | −11.298 | −0.2868 | −0.2341 | −0.3011 | −0.4863 |
| WP-14:SECT-S00155-80.69H-3.0R | 10.1 | −7.907 | −3.64 | −11.547 | −0.2898 | −0.2494 | −0.2954 | −0.4838 |
| WP-14:SECT-S00155-80.69H-4.5R | 10.12 | −7.994 | −3.691 | −11.684 | −0.2896 | −0.2391 | −0.2953 | −0.4801 |
| WP-14:SECT-S00155-80.94H-2.5R | 10.12 | −7.936 | −3.629 | −11.565 | −0.2924 | −0.2416 | −0.2924 | −0.4808 |
| WP-14:SECT-S00402-43.12H-4.0R | 10.05 | −7.314 | −3.331 | −10.644 | −0.272 | −0.2128 | −0.2427 | −0.4701 |
| WP-14:SECT-S00402-43.62H-1.5R | 10.03 | −7.595 | −3.587 | −11.182 | −0.2632 | −0.2136 | −0.253 | −0.4704 |
| WP-14:SECT-S00402-43.62H-11.5R | 10 | −7.429 | −3.484 | −10.914 | −0.2669 | −0.2132 | −0.2415 | −0.4689 |

TABLE VI-continued pH, Free Energies of Hydration ($\Delta G_p$, $\Delta G_a$, and $\Delta G_f$), and PCT (ASTM C1285-94) Normalized Release Rates for DWPF "Model Validation Data"

| | | kcal/100 g glass | | | $\log_{10}$ [NC$_i$(g/L)] | | | |
|---|---|---|---|---|---|---|---|---|
| Sample | pH | $\Delta G_p$ | $\dfrac{100}{MW}\Delta G_a^{WA}$ | $\Delta G_f$ | B | Li | Na | Si |
| WP-14:SECT-S00402-43.87H-6.0R | 10.02 | −7.514 | −3.455 | −10.969 | −0.2691 | −0.213 | −0.246 | −0.4719 |
| WP-14:SECT-S00402-62.68H-12.0R | 10.06 | −7.708 | −3.458 | −11.166 | −0.2596 | −0.1976 | −0.2573 | −0.4461 |
| WP-14:SECT-S00402-62.68H-9.5R | 10.06 | −7.705 | −3.527 | −11.233 | −0.248 | −0.1936 | −0.2414 | −0.4445 |
| WP-14:SECT-S00402-63.43H-4.5R | 10.06 | −7.629 | −3.445 | −11.075 | −0.2705 | −0.2162 | −0.2621 | −0.4586 |
| WP-14:SECT-S00402-63.43H-5.0R | 10.08 | −7.755 | −3.502 | −11.257 | −0.2453 | −0.1938 | −0.2451 | −0.4403 |
| WP-14:SECT-S00402-84.68H-12.0R | 10.09 | −7.739 | −3.47 | −11.209 | −0.2673 | −0.2147 | −0.2424 | −0.4414 |
| WP-14:SECT-S00402-87.93H-5.0R | 10.09 | −7.765 | −3.539 | −11.304 | −0.2467 | −0.1902 | −0.2473 | −0.4466 |
| WP-14:SECT-S00402-88.18H-1.25R | 10.11 | −7.374 | −3.204 | −10.578 | −0.2443 | −0.1901 | −0.2154 | −0.4431 |
| WP-14:SECT-S00402-88.43H-4.0R | 10.1 | −7.744 | −3.445 | −11.189 | −0.2448 | −0.1942 | −0.2482 | −0.4417 |
| WP-14:WALL-S00162-58.5H-2.0R | 10.18 | −8.051 | −3.604 | −11.655 | −0.2649 | −0.2171 | −0.2785 | −0.4588 |
| WP-15:GRAB-S00007 | 10.08 | −8.949 | −3.905 | −12.854 | −0.1366 | −0.0824 | −0.0603 | −0.35 |
| WP-15:GRAB-S00138 | 10.4 | −8.649 | −3.842 | −12.49 | −0.2555 | −0.1908 | −0.2052 | −0.4359 |
| WP-15:GRAB-S00163 | 10.19 | −7.829 | −3.393 | −11.222 | −0.2649 | −0.1991 | −0.2278 | −0.4728 |
| WP-15:GRAB-S00164 | 10.07 | −8.134 | −3.423 | −11.557 | −0.2241 | −0.1741 | −0.2183 | −0.4478 |
| WP-15:GRAB-S00165 | 10.19 | −8.36 | −3.539 | −11.899 | −0.2491 | −0.1887 | −0.2173 | −0.4559 |
| WP-15:GRAB-S00168 | 10.01 | −9.348 | −4.111 | −13.459 | −0.1452 | −0.0846 | −0.101 | −0.3665 |
| WP-15:GRAB-S00169 | 10.41 | −8.94 | −3.914 | −12.855 | −0.1748 | −0.1339 | −0.1498 | −0.398 |
| WP-15:GRAB-S00171 | 10.08 | −9.259 | −4.428 | −13.687 | −0.1518 | −0.1147 | −0.0873 | −0.3802 |
| WP-15:GRAB-S00174 | 10.14 | −9.326 | −4.278 | −13.604 | −0.0988 | −0.0575 | −0.0476 | −0.3533 |
| WP-15:GRAB-S00175 | 10.14 | −9.03 | −3.917 | −12.948 | −0.1289 | −0.0765 | −0.0589 | −0.3665 |
| WP-15:GRAB-S00176 | 10.37 | −9.091 | −4.133 | −13.224 | −0.145 | −0.1248 | −0.0929 | −0.3873 |
| WP-15:GRAB-S00177 | 10.44 | −9.301 | −4.105 | −13.407 | −0.0912 | −0.072 | −0.0496 | −0.3533 |
| WP-15:GRAB-S00178 | 10.51 | −9.399 | −4.244 | −13.643 | −0.0453 | −0.0278 | −0.014 | −0.3128 |
| WP-15:GRAB-S00179 | 10.53 | −9.494 | −4.276 | −13.769 | −0.0494 | −0.0324 | −0.0134 | −0.3128 |
| WP-15:GRAB-S00181 | 10.55 | −9.468 | −4.396 | −13.865 | −0.0544 | −0.0486 | −0.0134 | −0.3188 |
| WP-15:GRAB-S00200 | 10.3 | −8.353 | −3.664 | −12.018 | −0.2289 | −0.1658 | −0.1834 | −0.4478 |
| WP-15:GRAB-S00407 | 10.41 | −9.668 | −4.429 | −14.098 | −0.1273 | −0.1026 | −0.1034 | −0.3837 |
| WP-15:SECT-S00161-36.88H-03.50R | 10.45 | −7.584 | −3.614 | −11.198 | −0.2914 | −0.2404 | −0.2494 | −0.4904 |
| WP-15:SECT-S00161-36.88H-11.00R | 10.42 | −7.524 | −3.52 | −11.043 | −0.2967 | −0.2429 | −0.257 | −0.4815 |
| WP-15:SECT-S00161-37.63H-04.00R | 10.41 | −7.648 | −3.625 | −11.274 | −0.2973 | −0.248 | −0.2647 | −0.4904 |
| WP-15:SECT-S00161-37.88H-04.00R | 10.44 | −7.53 | −3.55 | −11.08 | −0.2969 | −0.2476 | −0.2561 | −0.4949 |
| WP-15:SECT-S00161-62.63H-07.00R | 10.38 | −7.752 | −3.662 | −11.414 | −0.2984 | −0.2565 | −0.2578 | −0.4949 |
| WP-15:SECT-S00161-63.13H-11.75R | 10.35 | −7.475 | −3.586 | −11.061 | −0.3034 | −0.2367 | −0.2356 | −0.495 |
| WP-15:SECT-S00161-63.38H-02.00R | 10.47 | −7.562 | −3.564 | −11.126 | −0.2629 | −0.2121 | −0.2179 | −0.4685 |
| WP-15:SECT-S00161-63.63H-07.00R | 10.41 | −7.744 | −3.671 | −11.415 | −0.2926 | −0.2486 | −0.2538 | −0.4949 |
| WP-15:SECT-S00161-90.51H-12.00R | 10.34 | −8.596 | −3.932 | −12.528 | −0.2634 | −0.1944 | −0.2858 | −0.4559 |
| WP-15:SECT-S00161-91.51H-02.00R | 10.34 | −8.186 | −3.381 | −11.566 | −0.2526 | −0.1805 | −0.2213 | −0.4437 |
| WP-15:SECT-S00161-92.51H-02.50R | 10.29 | −8.132 | −3.456 | −11.588 | −0.2576 | −0.1839 | −0.227 | −0.4559 |
| WP-15:SECT-S00161-92.76H-04.00R | 10.28 | −8.135 | −3.47 | −11.605 | −0.2623 | −0.2096 | −0.2634 | −0.4519 |
| WP-15:SECT-S00163-25.87H-02.50R | 10.16 | −7.966 | −3.452 | −11.417 | −0.2698 | −0.2185 | −0.2551 | −0.4859 |
| WP-15:SECT-S00163-26.75H-02.75R | 10.14 | −7.987 | −3.365 | −11.352 | −0.2852 | −0.2262 | −0.2688 | −0.4859 |
| WP-15:SECT-S00163-26.87H-11.00R | 10.15 | −8.052 | −3.472 | −11.524 | −0.3003 | −0.2491 | −0.2839 | −0.4949 |
| WP-15:SECT-S00163-27.00H-04.25R | 10.16 | −8.06 | −3.431 | −11.491 | −0.2671 | −0.2122 | −0.2476 | −0.4686 |
| WP-15:SECT-S00163-56.84H-04.00R | 10.25 | −8.019 | −3.535 | −11.555 | −0.2625 | −0.2151 | −0.2473 | −0.4685 |
| WP-15:SECT-S00163-57.09H-10.50R | 10.23 | −7.94 | −3.4 | −11.34 | −0.2645 | −0.2106 | −0.25 | −0.4685 |
| WP-15:SECT-S00163-57.34H-04.50R | 10.26 | −8.025 | −3.537 | −11.562 | −0.2545 | −0.2006 | −0.2447 | −0.4685 |
| WP-15:SECT-S00163-57.34H-05.75R | 10.16 | −7.89 | −3.435 | −11.325 | −0.2831 | −0.2351 | −0.2637 | −0.4815 |
| WP-15:SECT-S00163-71.28H-05.00R | 10.25 | −8.015 | −3.513 | −11.528 | −0.2821 | −0.2266 | −0.2336 | −0.4772 |
| WP-15:SECT-S00163-71.28H-09.75R | 10.26 | −7.977 | −3.528 | −11.505 | −0.2844 | −0.2306 | −0.234 | −0.4772 |
| WP-15:SECT-S00163-71.53H-02.50R | 10.27 | −8.088 | −3.767 | −11.855 | −0.2737 | −0.2132 | −0.2317 | −0.4728 |
| WP-15:SECT-S00163-71.78H-01.75R | 10.26 | −8.192 | −3.654 | −11.846 | −0.2871 | −0.2333 | −0.2465 | −0.4772 |
| WP-15:SECT-S00164-18.56H-03.00R | 10.05 | −8.755 | −3.695 | −12.45 | −0.2679 | −0.2224 | −0.2623 | −0.4559 |
| WP-15:SECT-S00164-18.81H-04.25R | 10.08 | −8.577 | −3.494 | −12.071 | −0.257 | −0.2153 | −0.2458 | −0.4519 |
| WP-15:SECT-S00164-18.94H-02.50R | 10.13 | −8.85 | −3.685 | −12.535 | −0.2423 | −0.1948 | −0.2431 | −0.4397 |
| WP-15:SECT-S00164-19.06H-11.75R | 10.07 | −8.683 | −3.54 | −12.223 | −0.2697 | −0.2248 | −0.2622 | −0.4478 |
| WP-15:SECT-S00164-46.19H-08.00R | 10.13 | −8.252 | −3.609 | −11.861 | −0.2719 | −0.2246 | −0.2564 | −0.4728 |
| WP-15:SECT-S00164-47.19H-02.50R | 10.16 | −8.317 | −3.633 | −11.95 | −0.2572 | −0.2105 | −0.2406 | −0.4559 |
| WP-15:SECT-S00164-47.44H-02.50R | 10.12 | −8.391 | −3.634 | −12.025 | −0.2642 | −0.2059 | −0.2517 | −0.4601 |
| WP-15:SECT-S00164-47.44H-03.50R | 10.05 | −8.273 | −3.58 | −11.853 | −0.2496 | −0.1959 | −0.2358 | −0.4519 |
| WP-15:SECT-S00164-72.88H-10.50R | 10.07 | −8.294 | −3.64 | −11.934 | −0.2766 | −0.2282 | −0.2602 | −0.4728 |
| WP-15:SECT-S00164-73.13H-02.50R | 10.05 | −8.221 | −3.514 | −11.735 | −0.2662 | −0.24 | −0.24 | −0.4601 |
| WP-15:SECT-S00164-73.38H-02.50R | 10.06 | −8.273 | −3.584 | −11.857 | −0.2688 | −0.2114 | −0.2318 | −0.4643 |
| WP-15:SECT-S00164-73.88H-02.00R | 10.06 | −8.231 | −3.549 | −11.78 | −0.2552 | −0.2018 | −0.2288 | −0.4559 |
| WP-15:SECT-S00179-22.38H-07.00R | 10.41 | −9.8 | −4.61 | −14.41 | −0.0813 | −0.0634 | −0.0723 | −0.3373 |
| WP-15:SECT-S00179-22.38H-10.75R | 10.4 | −9.712 | −4.641 | −14.353 | −0.1096 | −0.0895 | −0.0922 | −0.35 |
| WP-15:SECT-S00179-22.50H-03.00R | 10.41 | −9.866 | −4.672 | −14.539 | −0.1091 | −0.0913 | −0.0967 | −0.3468 |
| WP-15:SECT-S00179-22.76H-05.63R | 10.39 | −10.042 | −4.746 | −14.788 | −0.0976 | −0.0827 | −0.0919 | −0.3405 |
| WP-15:SECT-S00179-61.38H-07.00R | 10.43 | −9.422 | −4.292 | −13.713 | −0.0834 | −0.0561 | −0.0448 | −0.3281 |
| WP-15:SECT-S00179-61.51H-11.00R | 10.38 | −9.266 | −4.137 | −13.403 | −0.0952 | −0.0764 | −0.0599 | −0.3468 |
| WP-15:SECT-S00179-61.63H-07.50R | 10.45 | −9.618 | −4.337 | −13.955 | −0.0492 | −0.0294 | −0.0221 | −0.2954 |
| WP-15:SECT-S00179-62.76H-03.75R | 10.42 | −9.654 | −4.507 | −14.161 | −0.0743 | −0.0527 | −0.0455 | −0.3188 |

TABLE VI-continued pH, Free Energies of Hydration ($\Delta G_p$, $\Delta G_a$, and $\Delta G_f$), and PCT (ASTM C1285-94) Normalized Release Rates for DWPF "Model Validation Data"

| | | | kcal/100 g glass | | | $\log_{10}$ [NC$_i$(g/L)] | | |
|---|---|---|---|---|---|---|---|---|
| Sample | pH | $\Delta G_p$ | $\frac{100}{MW} \Delta G_a^{WA}$ | $\Delta G_f$ | B | Li | Na | Si |
| WP-15:SECT-S00179-82.70H-12.00R | 10.49 | −10.065 | −4.719 | −14.784 | −0.0636 | −0.0516 | −0.0686 | −0.328 |
| WP-15:SECT-S00179-83.07H-03.00R | 10.43 | −9.936 | −4.725 | −14.661 | −0.0857 | −0.0753 | −0.0745 | −0.3404 |
| WP-15:SECT-S00179-83.20H-03.50R | 10.44 | −9.873 | −4.747 | −14.62 | −0.09 | −0.0671 | −0.0751 | −0.3404 |
| WP-15:SECT-S00179-83.32H-02.50R | 10.47 | −9.894 | −4.61 | −14.504 | −0.0909 | −0.0716 | −0.0778 | −0.3404 |
| WP-15:SECT-S00181-28.88H-12.00R | 10.49 | −9.455 | −4.445 | −13.9 | −0.092 | −0.0805 | −0.0515 | −0.3437 |
| WP-15:SECT-S00181-29.63H-06.00R | 10.47 | −9.379 | −4.349 | −13.728 | −0.0928 | −0.0728 | −0.0505 | −0.328 |
| WP-15:SECT-S00181-30.88H-01.25R | 10.45 | −9.483 | −4.375 | −13.858 | −0.1031 | −0.0908 | −0.0683 | −0.3436 |
| WP-15:SECT-S00181-31.13H-03.50R | 10.45 | −9.551 | −4.437 | −13.988 | −0.0995 | −0.0916 | −0.066 | −0.3404 |
| WP-15:SECT-S00181-56.38H-04.00R | 10.44 | −9.6 | −4.424 | −14.023 | −0.0963 | −0.0734 | −0.0655 | −0.3372 |
| WP-15:SECT-S00181-57.38H-03.00R | 10.46 | −9.917 | −4.491 | −14.408 | −0.0831 | −0.0619 | −0.0652 | −0.3188 |
| WP-15:SECT-S00181-57.38H-04.25R | 10.47 | −9.551 | −4.402 | −13.953 | −0.0759 | −0.0516 | −0.048 | −0.3218 |
| WP-15:SECT-S00181-67.76H-06.00R | 10.43 | −9.603 | −4.387 | −13.99 | −0.0849 | −0.0822 | −0.0542 | −0.3279 |
| WP-15:SECT-S00181-68.01H-05.50R | 10.43 | −9.548 | −4.417 | −13.966 | −0.0698 | −0.0633 | −0.0447 | −0.3218 |
| WP-15:SECT-S00181-68.26H-12.00R | 10.46 | −9.558 | −4.459 | −14.017 | −0.0098 | −0.0345 | −0.025 | −0.3218 |
| WP-15:SECT-S00181-68.51H-03.00R | 10.43 | −9.438 | −4.435 | −13.873 | −0.0571 | −0.0534 | −0.027 | −0.3219 |
| WP-15:SECT-S00200-69.50H-12.00R | 10.24 | −9.406 | −3.931 | −13.337 | −0.2307 | −0.2039 | −0.2332 | −0.4358 |
| WP-15:SECT-S00407-33.94H-03.00R | 10.46 | −9.506 | −4.403 | −13.909 | −0.04 | −0.0256 | −0.0214 | −0.3128 |
| WP-15:SECT-S00407-34.19H-03.00R | 10.42 | −9.559 | −4.211 | −13.771 | −0.0843 | −0.0696 | −0.0607 | −0.3341 |
| WP-15:SECT-S00407-34.44H-12.00R | 10.5 | −9.595 | −4.446 | −14.041 | −0.0752 | −0.0626 | −0.0541 | −0.3373 |
| WP-15:SECT-S00407-34.69H-02.50R | 10.49 | −9.507 | −4.389 | −13.896 | −0.099 | −0.0844 | −0.0656 | −0.3469 |
| WP-15:SECT-S00407-63.44H-11.00R | 10.43 | −9.508 | −4.405 | −13.913 | −0.0668 | −0.0546 | −0.0361 | −0.331 |
| WP-15:SECT-S00407-63.69H-03.25R | 10.46 | −9.601 | −4.376 | −13.976 | −0.0598 | −0.0486 | −0.0355 | −0.3249 |
| WP-15:SECT-S00407-64.44H-04.00R | 10.51 | −9.596 | −4.458 | −14.054 | −0.0567 | −0.0399 | −0.0286 | −0.331 |
| WP-15:SECT-S00407-64.44H-08.00R | 10.45 | −9.566 | −4.41 | −13.976 | −0.0538 | −0.0503 | −0.049 | −0.3405 |
| WP-15:SECT-S00407-72.69H-04.50R | 10.45 | −9.601 | −4.453 | −14.054 | −0.0546 | −0.0419 | −0.0313 | −0.331 |
| WP-15:SECT-S00407-73.19H-08.50R | 10.44 | −9.453 | −4.299 | −13.752 | −0.0492 | −0.0401 | −0.0179 | −0.328 |
| WP-15:SECT-S00407-73.69H-02.00R | 10.48 | −9.619 | −4.366 | −13.986 | −0.0855 | −0.051 | −0.0369 | −0.3279 |
| WP-15:SECT-S00407-74.19H-04.25R | 10.48 | −9.514 | −4.424 | −13.938 | −0.0393 | −0.0283 | −0.0103 | −0.3188 |
| WP-15:WALL-S00007-66.25H-02.25R | 10.09 | −9.037 | −3.814 | −12.851 | −0.1505 | −0.0928 | −0.0881 | −0.3568 |
| WP-15:WALL-S00138-54.50H-05.00R | 10.57 | −8.382 | −3.703 | −12.084 | −0.2269 | −0.1702 | −0.1725 | −0.4319 |
| WP-15:WALL-S00165-87.50H-02.25R | 10.24 | −8.621 | −3.726 | −12.347 | −0.2632 | −0.2149 | −0.2416 | −0.4643 |
| WP-15:WALL-S00168-93.50H-02.25R | 10.05 | −9.416 | −4.261 | −13.677 | −0.1761 | −0.1202 | −0.1367 | −0.3802 |
| WP-15:WALL-S00169-84.50H-02.50R | 10.37 | −9.133 | −4.317 | −13.45 | −0.2135 | −0.1755 | −0.2011 | −0.428 |
| WP-15:WALL-S00170-50.50H-01.50R | 10.62 | −9.001 | −3.965 | −12.965 | −0.2088 | −0.1608 | −0.1608 | −0.4127 |
| WP-15:WALL-S00171-77.00H-02.00R | 10.12 | −9.131 | −4.917 | −14.048 | −0.1769 | −0.1397 | −0.1022 | −0.3944 |
| WP-15:WALL-S00172-61.00H-02.25R | 10.11 | −9.846 | −4.312 | −14.158 | −0.1297 | −0.0991 | −0.1049 | −0.3632 |
| WP-15:WALL-S00174-72.00H-02.00R | 10.15 | −9.123 | −4.083 | −13.206 | −0.0921 | −0.0467 | −0.0355 | −0.3437 |
| WP-15:WALL-S00175-57.00H-02.13R | 10.13 | −9.208 | −4.114 | −13.322 | −0.1165 | −0.0821 | −0.0661 | −0.3533 |
| WP-15:WALL-S00176-63.50H-02.00R | 10.48 | −9.411 | −4.198 | −13.609 | −0.1189 | −0.0999 | −0.0859 | −0.3565 |
| WP-15:WALL-S00177-66.50H-01.50R | 10.37 | −9.456 | −4.241 | −13.697 | −0.1193 | −0.0938 | −0.0894 | −0.3565 |
| WP-15:WALL-S00178-71.50H-01.75R | 10.47 | −9.301 | −4.156 | −13.457 | −0.1008 | −0.07 | −0.0614 | −0.3373 |
| WP-16:GRAB-S00182 | 10.41 | −9.537 | −4.473 | −14.010 | −0.0933 | −0.0740 | −0.0331 | |
| WP-16:GRAB-S00184 | 10.56 | −9.681 | −5.234 | −14.915 | −0.2953 | −0.2100 | −0.2100 | |
| WP-16:GRAB-S00187 | 10.47 | −9.609 | −4.561 | −14.170 | −0.1193 | −0.0846 | −0.0491 | |
| WP-16:GRAB-S00188 | 10.73 | −10.313 | −5.606 | −15.919 | −0.1591 | −0.1116 | −0.0951 | |
| WP-16:GRAB-S00190 | 10.45 | −9.852 | −4.966 | −14.817 | −0.1961 | −0.1328 | −0.1173 | |
| WP-16:GRAB-S00193 | 10.50 | −10.189 | −5.389 | −15.579 | −0.2292 | −0.1827 | −0.1591 | |
| WP-16:GRAB-S00195 | 10.52 | −10.402 | −5.609 | −16.011 | −0.2316 | −0.1612 | −0.1675 | |
| WP-16:GRAB-S00196 | 10.52 | −10.479 | −5.748 | −16.226 | −0.2468 | −0.1591 | −0.1894 | |
| WP-16:GRAB-S00197 | 10.74 | −9.976 | −5.237 | −15.213 | −0.2267 | −0.1508 | −0.1427 | |
| WP-16:GRAB-S00199 | 10.42 | −10.153 | −5.047 | −15.201 | −0.1827 | −0.1308 | −0.1211 | |
| WP-16:GRAB-S00208 | 10.48 | −10.725 | −5.889 | −16.614 | −0.1783 | −0.1173 | −0.1387 | |
| WP-16:GRAB-S00210 | 10.41 | −9.940 | −4.930 | −14.870 | −0.1250 | −0.0827 | −0.0655 | |
| WP-16:GRAB-S00404 | 10.42 | −10.192 | −5.272 | −15.464 | −0.0726 | −0.0541 | −0.0444 | |
| WP-16:GRAB-S00405 | 10.49 | −10.311 | −5.634 | −15.945 | −0.2519 | −0.1718 | −0.1894 | |
| WP-16:GRAB-S00408 | 10.49 | −9.723 | −5.399 | −15.122 | −0.2730 | −0.1783 | −0.1783 | |
| WP-16:GRAB-S00410 | 10.39 | −9.872 | −5.272 | −15.144 | −0.2730 | −0.1916 | −0.1984 | |
| WP-16:GRAB-S00412 | 10.56 | −10.353 | −5.546 | −15.900 | −0.1230 | −0.0844 | −0.0638 | |
| WP-16:SECT-S00182-15.50H-12.00R | 10.45 | −9.600 | −4.576 | −14.176 | −0.0838 | −0.0639 | −0.0379 | |
| WP-16:SECT-S00182-16.00H-03.30R | 10.40 | −9.477 | −4.494 | −13.971 | −0.0898 | −0.0689 | −0.0442 | |
| WP-16:SECT-S00182-16.25H-01.75R | 10.41 | −9.487 | −4.436 | −13.924 | −0.0828 | −0.0706 | −0.0332 | |
| WP-16:SECT-S00182-17.00H-03.00R | 10.43 | −9.422 | −4.375 | −13.797 | −0.0809 | −0.0639 | −0.0315 | |
| WP-16:SECT-S00182-41.50H-02.50R | 10.40 | −9.652 | −4.741 | −14.393 | −0.1098 | −0.0638 | −0.0539 | |
| WP-16:SECT-S00182-41.50H-07.00R | 10.44 | −9.581 | −4.815 | −14.396 | −0.1081 | −0.0622 | −0.0442 | |
| WP-16:SECT-S00182-42.00H-04.50R | 10.39 | −9.644 | −4.718 | −14.362 | −0.1061 | −0.0605 | −0.0490 | |
| WP-16:SECT-S00182-42.00H-11.50R | 10.40 | −9.799 | −4.922 | −14.721 | −0.1117 | −0.0740 | −0.0689 | |
| WP-16:SECT-S00182-73.13H-11.50R | 10.40 | −9.637 | −4.549 | −14.186 | −0.0556 | −0.0426 | −0.0178 | |
| WP-16:SECT-S00182-73.38H-02.75R | 10.43 | −9.609 | −4.523 | −14.133 | −0.0689 | −0.0522 | −0.0238 | |
| WP-16:SECT-S00182-73.63H-04.25R | 10.42 | −9.777 | −4.675 | −14.452 | −0.0706 | −0.0539 | −0.0254 | |
| WP-16:SECT-S00182-73.88H-02.00R | 10.45 | −9.765 | −4.774 | −14.540 | −0.0589 | −0.0362 | −0.0163 | |
| WP-16:SECT-S00184-29.00H-10.00R | 10.62 | −9.784 | −5.228 | −15.011 | −0.2925 | −0.2054 | −0.2171 | |

TABLE VI-continued pH, Free Energies of Hydration ($\Delta G_p$, $\Delta G_a$, and $\Delta G_f$), and PCT (ASTM C1285-94) Normalized Release Rates for DWPF "Model Validation Data"

| | | kcal/100 g glass | | | $\log_{10}$ [NC$_i$(g/L)] | | | |
|---|---|---|---|---|---|---|---|---|
| Sample | pH | $\Delta G_p$ | $\frac{100}{MW} \Delta G_a^{WA}$ | $\Delta G_f$ | B | Li | Na | Si |
| WP-16:SECT-S00184-29.50H-04.00R | 10.58 | −9.683 | −5.165 | −14.847 | −0.3098 | −0.2218 | −0.2291 | |
| WP-16:SECT-S00184-30.50H-04.00R | 10.55 | −9.698 | −5.204 | −14.902 | −0.3098 | −0.2218 | −0.2366 | |
| WP-16:SECT-S00184-30.50H-06.00R | 10.58 | −9.722 | −5.088 | −14.810 | −0.2785 | −0.1939 | −0.2124 | |
| WP-16:SECT-S00184-60.25H-05.00R | 10.53 | −9.860 | −5.337 | −15.198 | −0.3279 | −0.2467 | −0.2544 | |
| WP-16:SECT-S00184-61.00H-03.00R | 10.58 | −9.729 | −5.189 | −14.918 | −0.2953 | −0.2100 | −0.2171 | |
| WP-16:SECT-S00184-61.25H-11.50R | 10.57 | −9.822 | −5.250 | −15.073 | −0.3040 | −0.2219 | −0.2316 | |
| WP-16:SECT-S00184-61.50H-05.00R | 10.59 | −9.759 | −5.207 | −14.966 | −0.3128 | −0.2292 | −0.2391 | |
| WP-16:SECT-S00184-77.75H-03.00R | 10.52 | −10.063 | −5.493 | −15.556 | −0.3098 | −0.2267 | −0.2492 | |
| WP-16:SECT-S00184-77.75H-10.00R | 10.52 | −10.613 | −6.012 | −16.625 | −0.2953 | −0.2076 | −0.2544 | |
| WP-16:SECT-S00184-79.00H-04.00R | 10.46 | −10.197 | −5.594 | −15.791 | −0.3128 | −0.2267 | −0.2544 | |
| WP-16:SECT-S00184-79.25H-03.50R | 10.50 | −10.359 | −5.827 | −16.186 | −0.2928 | −0.2057 | −0.2446 | |
| WP-16:SECT-S00194-14.75H-06.00R | 10.64 | −10.048 | −5.335 | −15.384 | −0.2924 | −0.2171 | −0.2291 | |
| WP-16:SECT-S00194-15.25H-11.75R | 10.65 | −9.621 | −4.806 | −14.427 | −0.2812 | −0.2080 | −0.1938 | |
| WP-16:SECT-S00194-15.50H-01.50R | 10.63 | −9.612 | −4.993 | −14.605 | −0.2868 | −0.2100 | −0.2076 | |
| WP-16:SECT-S00194-15.50H-06.50R | 10.67 | −9.713 | −5.052 | −14.765 | −0.2757 | −0.2030 | −0.1984 | |
| WP-16:SECT-S00194-52.50H-06.50R | 10.62 | −9.875 | −5.329 | −15.203 | −0.3040 | −0.2243 | −0.2417 | |
| WP-16:SECT-S00194-53.00H-05.00R | 10.62 | −9.567 | −5.154 | −14.720 | −0.2953 | −0.2171 | −0.2195 | |
| WP-16:SECT-S00194-53.00H-07.50R | 10.61 | −9.822 | −5.349 | −15.170 | −0.2953 | −0.2147 | −0.2341 | |
| WP-16:SECT-S00194-53.50H-11.50R | 10.60 | −9.804 | −5.279 | −15.084 | −0.2868 | −0.2076 | −0.2316 | |
| WP-16:SECT-S00194-80.63H-02.50R | 10.60 | −9.890 | −5.288 | −15.178 | −0.3099 | −0.2342 | −0.2442 | |
| WP-16:SECT-S00194-81.13H-09.50R | 10.54 | −10.017 | −5.530 | −15.547 | −0.3188 | −0.2416 | −0.2596 | |
| WP-16:SECT-S00194-81.38H-03.00R | 10.60 | −9.786 | −5.155 | −14.942 | −0.3098 | −0.2243 | −0.2391 | |
| WP-16:SECT-S00194-81.63H-03.50R | 10.58 | −10.047 | −5.463 | −15.511 | −0.3069 | −0.2267 | −0.2518 | |
| WP-16:SECT-S00210-31.38H-11.50R | 10.43 | −10.453 | −5.557 | −16.010 | −0.0988 | −0.0655 | −0.0775 | |
| WP-16:SECT-S00210-32.13H-05.00R | 10.40 | −10.167 | −5.273 | −15.440 | −0.0971 | −0.0639 | −0.0639 | |
| WP-16:SECT-S00210-32.38H-03.50R | 10.38 | −10.266 | −5.399 | −15.665 | −0.1212 | −0.0792 | −0.0863 | |
| WP-16:SECT-S00210-32.63H-05.25R | 10.37 | −10.098 | −5.198 | −15.296 | −0.1098 | −0.0757 | −0.0706 | |
| WP-16:SECT-S00210-49.51H-08.00R | 10.41 | −9.905 | −5.011 | −14.915 | −0.0915 | −0.0605 | −0.0523 | |
| WP-16:SECT-S00210-49.88H-01.50R | 10.39 | −10.274 | −5.380 | −15.654 | −0.1043 | −0.0672 | −0.0880 | |
| WP-16:SECT-S00210-49.88H-11.00R | 10.43 | −10.019 | −5.101 | −15.120 | −0.0915 | −0.0588 | −0.0588 | |
| WP-16:SECT-S00210-50.13H-04.00R | 10.43 | −10.033 | −5.058 | −15.091 | −0.1061 | −0.0655 | −0.0740 | |
| WP-16:SECT-S00210-68.76H-05.00R | 10.40 | −9.959 | −4.809 | −14.769 | −0.1211 | −0.0880 | −0.0689 | |
| WP-16:SECT-S00210-69.01H-02.00R | 10.43 | −10.123 | −5.086 | −15.209 | −0.1006 | −0.0706 | −0.0638 | |
| WP-16:SECT-S00210-69.01H-11.25R | 10.47 | −9.968 | −4.898 | −14.866 | −0.0793 | −0.0491 | −0.0394 | |
| WP-16:SECT-S00210-69.26H-07.00R | 10.43 | −9.984 | −4.883 | −14.867 | −0.1024 | −0.0689 | −0.0572 | |
| WP-16:SECT-S00404-11.63H-04.25R | 10.40 | −9.790 | −4.919 | −14.709 | −0.1006 | −0.0588 | −0.0490 | |
| WP-16:SECT-S00404-11.75H-03.00R | 10.34 | −9.782 | −4.838 | −14.621 | −0.1211 | −0.0757 | −0.0706 | |
| WP-16:SECT-S00404-11.88H-05.00R | 10.38 | −9.675 | −4.749 | −14.424 | −0.1098 | −0.0656 | −0.0474 | |
| WP-16:SECT-S00404-12.63H-10.50R | 10.39 | −9.667 | −4.788 | −14.455 | −0.0828 | −0.0426 | −0.0269 | |
| WP-16:SECT-S00404-52.51H-06.00R | 10.39 | −9.982 | −5.122 | −15.103 | −0.0845 | −0.0706 | −0.0572 | |
| WP-16:SECT-S00404-53.01H-10.00R | 10.40 | −10.004 | −5.153 | −15.157 | −0.0827 | −0.0740 | −0.0622 | |
| WP-16:SECT-S00404-54.01H-04.00R | 10.40 | −9.770 | −4.922 | −14.692 | −0.0844 | −0.0723 | −0.0490 | |
| WP-16:SECT-S00404-54.01H-04.25R | 10.38 | −9.999 | −5.120 | −15.119 | −0.1024 | −0.0827 | −0.0689 | |
| WP-16:SECT-S00404-74.26H-02.25R | 10.46 | −10.168 | −5.342 | −15.510 | −0.0933 | −0.0740 | −0.0639 | |
| WP-16:SECT-S00404-74.51H-02.00R | 10.48 | −9.779 | −4.950 | −14.728 | −0.0809 | −0.0689 | −0.0378 | |
| WP-16:SECT-S00404-74.76H-04.50R | 10.46 | −10.060 | −5.176 | −15.236 | −0.0969 | −0.0792 | −0.0605 | |
| WP-16:SECT-S00404-75.51H-02.75R | 10.44 | −9.884 | −5.042 | −14.926 | −0.0792 | −0.0656 | −0.0410 | |
| WP-16:SECT-S00408-19.75H-06.00R | 10.45 | −9.724 | −5.366 | −15.090 | −0.2982 | −0.2100 | −0.2171 | |
| WP-16:SECT-S00408-20.75H-03.00R | 10.49 | −9.696 | −5.300 | −14.996 | −0.2925 | −0.2076 | −0.2147 | |
| WP-16:SECT-S00408-20.75H-10.00R | 10.53 | −9.728 | −5.271 | −14.999 | −0.2870 | −0.1917 | −0.2009 | |
| WP-16:SECT-S00408-21.25H-03.00R | 10.48 | −9.623 | −5.192 | −14.815 | −0.2731 | −0.1849 | −0.1984 | |
| WP-16:SECT-S00408-47.25H-03.00R | 10.42 | −9.638 | −5.167 | −14.804 | −0.3279 | −0.2416 | −0.2416 | |
| WP-16:SECT-S00408-47.25H-12.00R | 10.45 | −9.588 | −5.168 | −14.756 | −0.3040 | −0.2148 | −0.2243 | |
| WP-16:SECT-S00408-47.75H-03.00R | 10.52 | −9.606 | −5.234 | −14.840 | −0.2841 | −0.1939 | −0.2053 | |
| WP-16:SECT-S00408-47.75H-05.00R | 10.48 | −9.685 | −5.312 | −14.997 | −0.3070 | −0.2148 | −0.2342 | |
| WP-16:SECT-S00408-77.13H-05.00R | 10.43 | −9.881 | −5.468 | −15.349 | −0.3128 | −0.2316 | −0.2316 | |
| WP-16:SECT-S00408-77.63H-05.00R | 10.46 | −9.695 | −5.299 | −14.993 | −0.3098 | −0.2267 | −0.2267 | |
| WP-16:SECT-S00408-78.63H-02.50R | 10.47 | −9.802 | −5.416 | −15.218 | −0.3218 | −0.2442 | −0.2467 | |
| WP-16:SECT-S00408-78.63H-09.75R | 10.45 | −9.714 | −5.371 | −15.085 | −0.3098 | −0.2316 | −0.2291 | |
| WP-16:WALL-S00187-77.25H-02.00R | 10.48 | −9.665 | −4.620 | −14.285 | −0.1080 | −0.0810 | −0.0458 | |
| WP-16:WALL-S00188-56.00H-03.00R | 10.63 | −10.179 | −5.466 | −15.644 | −0.1783 | −0.1308 | −0.1135 | |
| WP-16:WALL-S00190-58.00H-02.25R | 10.46 | −10.044 | −5.180 | −15.224 | −0.1654 | −0.1135 | −0.1042 | |
| WP-16:WALL-S00193-52.50H-01.75R | 10.48 | −10.215 | −5.469 | −15.684 | −0.2147 | −0.1783 | −0.1633 | |
| WP-16:WALL-S00195-62.00H-01.50R | 10.49 | −10.524 | −5.678 | −16.202 | −0.2544 | −0.1827 | −0.2030 | |
| WP-16:WALL-S00196-72.00H-01.75R | 10.54 | −10.629 | −5.886 | −16.515 | −0.2391 | −0.1612 | −0.2053 | |
| WP-16:WALL-S00197-93.50H-01.25R | 10.63 | −9.949 | −5.226 | −15.175 | −0.2366 | −0.1633 | −0.1654 | |
| WP-16:WALL-S00199-68.00H-02.75R | 10.46 | −10.379 | −5.358 | −15.736 | −0.1938 | −0.1347 | −0.1367 | |
| WP-16:WALL-S00206-59.00H-02.50R | 10.64 | −9.735 | −5.330 | −15.066 | −0.2868 | −0.2100 | −0.2171 | |
| WP-16:WALL-S00208-69.00H-01.50R | 10.50 | −10.834 | −5.940 | −16.774 | −0.1740 | −0.1061 | −0.1427 | |
| WP-16:WALL-S00405-73.00H-01.75R | 10.48 | −10.424 | −5.828 | −16.252 | −0.2649 | −0.1805 | −0.2171 | |
| WP-16:WALL-S00410-30.50H-02.75R | 10.39 | −9.967 | −5.370 | −15.337 | −0.2649 | −0.1849 | −0.2076 | |

TABLE VI-continued pH, Free Energies of Hydration ($\Delta G_p$, $\Delta G_a$, and $\Delta G_f$), and PCT (ASTM C1285-94) Normalized Release Rates for DWPF "Model Validation Data"

| | | kcal/100 g glass | | | $\log_{10}$ [NC$_i$(g/L)] | | | |
|---|---|---|---|---|---|---|---|---|
| Sample | pH | $\Delta G_p$ | $\frac{100}{MW} \Delta G_a^{WA}$ | $\Delta G_f$ | B | Li | Na | Si |
| WP-16:WALL-S00412-53.00H-02.50R | 10.55 | −10.364 | −5.546 | −15.910 | −0.1549 | −0.1135 | −0.0969 | |
| WP-17:GRAB-S00303 | 10.33 | −10.357 | −6.139 | −16.496 | −0.2819 | −0.2129 | −0.2632 | |
| WP-17:GRAB-S00306 | 10.58 | −10.146 | −5.718 | −15.863 | −0.2801 | −0.2114 | −0.2386 | |
| WP-17:GRAB-S00310 | 10.20 | −10.050 | −5.619 | −15.669 | −0.2187 | −0.1584 | −0.1866 | |
| WP-17:GRAB-S00318 | 10.59 | −9.961 | −5.508 | −15.468 | −0.2840 | −0.2097 | −0.2240 | |
| WP-17:GRAB-S00319 | 10.73 | −9.974 | −5.851 | −15.555 | −0.2738 | −0.2051 | −0.2245 | |
| WP-17:GRAB-S00406 | 10.58 | −10.010 | −5.798 | −15.808 | −0.2947 | −0.2137 | −0.2346 | |
| WP-17:GRAB-S00411 | 10.59 | −9.972 | −5.744 | −15.716 | −0.2717 | −0.2032 | −0.2211 | |
| WP-17:GRAB-S00413 | 10.69 | −9.920 | −5.301 | −15.221 | −0.2596 | −0.1938 | −0.2147 | |
| WP-17:SECT-S00303-17.25H-11.50R | 10.33 | −9.711 | −5.565 | −15.277 | −0.2944 | −0.2233 | −0.2434 | |
| WP-17:SECT-S00303-17.50H-04.50R | 10.34 | −9.836 | −5.650 | −15.487 | −0.2933 | −0.2214 | −0.2439 | |
| WP-17:SECT-S00303-17.75H-02.50R | 10.32 | −9.745 | −5.653 | −15.398 | −0.3010 | −0.2306 | −0.2536 | |
| WP-17:SECT-S00303-18.50H-03.00R | 10.36 | −9.968 | −5.741 | −15.709 | −0.2871 | −0.2163 | −0.2510 | |
| WP-17:SECT-S00303-44.00H-03.00R | 10.34 | −10.337 | −6.264 | −16.601 | −0.2787 | −0.2182 | −0.2738 | |
| WP-17:SECT-S00303-44.25H-02.75R | 10.35 | −10.189 | −5.959 | −16.148 | −0.2812 | −0.2175 | −0.2676 | |
| WP-17:SECT-S00303-45.00H-03.00R | 10.34 | −10.200 | −6.032 | −16.232 | −0.2893 | −0.2274 | −0.2757 | |
| WP-17:SECT-S00303-45.25H-11.50R | 10.40 | −10.077 | −5.936 | −16.012 | −0.2854 | −0.2253 | −0.2684 | |
| WP-17:SECT-S00303-54.75H-11.50R | 10.37 | −9.886 | −5.840 | −15.726 | −0.3025 | −0.2299 | −0.2657 | |
| WP-17:SECT-S00303-56.25H-06.25R | 10.38 | −9.921 | −5.762 | −15.683 | −0.3137 | −0.2398 | −0.2711 | |
| WP-17:SECT-S00303-56.75H-03.50R | 10.33 | −9.863 | −5.703 | −15.567 | −0.3095 | −0.2324 | −0.2633 | |
| WP-17:SECT-S00303-57.00H-03.00R | 10.38 | −9.933 | −5.718 | −15.650 | −0.2950 | −0.2252 | −0.2560 | |
| WP-17:SECT-S00310-24.00H-09.50R | 10.13 | −10.021 | −5.744 | −15.765 | −0.3096 | −0.2271 | −0.2589 | |
| WP-17:SECT-S00310-24.50H-03.50R | 10.15 | −9.945 | −5.551 | −15.496 | −0.3034 | −0.2233 | −0.2498 | |
| WP-17:SECT-S00310-25.25H-04.25R | 10.15 | −10.018 | −5.681 | −15.699 | −0.3152 | −0.2322 | −0.2589 | |
| WP-17:SECT-S00310-25.50H-05.00R | 10.12 | −10.015 | −5.712 | −15.727 | −0.3152 | −0.2378 | −0.2565 | |
| WP-17:SECT-S00310-48.88H-05.00R | 10.13 | −10.051 | −5.583 | −15.634 | −0.3043 | −0.2216 | −0.2568 | |
| WP-17:SECT-S00310-49.38H-02.25R | 10.14 | −10.047 | −5.711 | −15.757 | −0.3095 | −0.2324 | −0.2604 | |
| WP-17:SECT-S00310-49.38H-08.50R | 10.14 | −10.315 | −5.985 | −16.300 | −0.3155 | −0.2346 | −0.2765 | |
| WP-17:SECT-S00310-50.38H-04.00R | 10.11 | −10.054 | −5.696 | −15.750 | −0.3249 | −0.2366 | −0.2703 | |
| WP-17:SECT-S00310-61.26H-11.50R | 10.10 | −9.972 | −5.613 | −15.585 | −0.3203 | −0.2396 | −0.2730 | |
| WP-17:SECT-S00310-62.76H-05.00R | 10.12 | −9.898 | −5.481 | −15.379 | −0.3101 | −0.2257 | −0.2575 | |
| WP-17:SECT-S00310-62.76H-06.00R | 10.12 | −10.127 | −5.788 | −15.915 | −0.3074 | −0.2260 | −0.2689 | |
| WP-17:SECT-S00310-63.26H-03.00R | 10.13 | −9.933 | −5.559 | −15.492 | −0.2993 | −0.2228 | −0.2547 | |
| WP-17:SECT-S00409-44.00H-03.00R | 10.27 | −10.559 | −6.396 | −16.955 | −0.3158 | −0.2388 | −0.2879 | |
| WP-17:SECT-S00409-44.00H-04.00R | 10.30 | −10.712 | −6.627 | −17.339 | −0.3057 | −0.2314 | −0.2896 | |
| WP-17:SECT-S00409-44.25H-03.50R | 10.31 | −10.605 | −6.475 | −17.080 | −0.3304 | −0.2552 | −0.3028 | |
| WP-17:SECT-S00409-44.25H-11.00R | 10.29 | −10.550 | −6.443 | −16.992 | −0.3225 | −0.2425 | −0.2922 | |
| WP-17:SECT-S00409-61.13H-03.00R | 10.31 | −10.608 | −6.379 | −16.988 | −0.3087 | −0.2329 | −0.2877 | |
| WP-17:SECT-S00409-61.13H-0.500R | 10.40 | −10.490 | −6.333 | −16.823 | −0.3042 | −0.2279 | −0.2752 | |
| WP-17:SECT-S00409-61.13H-10.50R | 10.39 | −10.572 | −6.417 | −16.988 | −0.3182 | −0.2398 | −0.2896 | |
| WP-17:SECT-S00409-61.63H-03.50R | 10.34 | −10.313 | −6.196 | −16.509 | −0.3101 | −0.2383 | −0.2741 | |
| WP-17:SECT-S00409-75.38H-05.00R | 10.21 | −10.185 | −6.054 | −16.239 | −0.2999 | −0.2319 | −0.2854 | |
| WP-17:SECT-S00409-75.63H-04.50R | 10.22 | −10.295 | −6.158 | −16.453 | −0.3017 | −0.2342 | −0.2858 | |
| WP-17:SECT-S00409-76.13H-12.00R | 10.22 | −10.186 | −6.071 | −16.257 | −0.2851 | −0.2216 | −0.2690 | |
| WP-17:SECT-S00409-76.38H-04.25R | 10.25 | −10.182 | −6.113 | −16.295 | −0.2993 | −0.2285 | −0.2769 | |
| WP-17:WALL-S00306-48.50H-01.50R | 10.52 | −10.250 | −5.871 | −16.121 | −0.2854 | −0.2236 | −0.2542 | |
| WP-17:WALL-S00318-43.00H-01.50R | 10.52 | −9.796 | −5.379 | −15.175 | −0.2785 | −0.2171 | −0.2243 | |
| WP-17:WALL-S00319-45.50H-02.25R | 10.52 | −9.683 | −5.356 | −15.039 | −0.2933 | −0.2284 | −0.2373 | |
| WP-17:WALL-S00406-58.00H-02.00R | 10.54 | −9.977 | −5.435 | −15.412 | −0.2812 | −0.2219 | −0.2341 | |

A similar procedure may be followed to determine the aqueous solubility for fiberglass and other glasses where biosolubility is desired (and thus decreased durability and phase separation are desirable). The processes for making these glasses may be controlled by varying the feedstock until the method of the present invention described above indicates that the resulting glass composition will have the desired solubility and inhomogeneity characteristics using methods analogous to those described above.

The present invention having been thus described, it will be clear that the same can be varied or modified in many ways apparent to one of skill in the art. Such variations or modifications which do not depart from the spirit and scope of the present invention are included within the scope of the following claims.

What is claimed is:

1. A process for controlling production of glass, comprising:

A. monitoring production of glass by:

1. determining the composition of glass-forming feedstock materials to be fed to a melter;

2. determining one or more leachate concentrations of one or more components of a glass composition in an aqueous solution of said glass composition based upon said composition of said glass-forming feedstock materials thereby obtaining a one or more determined leachate concentrations by:

a. determining a final glass dissolution free energy change, $\Delta G_f$, comprising:

i. determining the pH of said aqueous solution of said glass composition;

ii. determining the free energy change associated with the dissociation of silicic acid or boric acid or both at said determined pH, $\Delta G_a^{WA}$;

iii. determining the free energy change associated with accelerated matrix dissolution at said determined PH, $\Delta G_a^{SB}$; and iv. summing said $\Delta G_a^{WA}$ and said $\Delta G_a^{SB}$ to obtain $\Delta G_a$, and v. determining a preliminary glass dissolution estimator, $\Delta G_p$, b. summing said $\Delta G_p$ and said $\Delta G_a$ to obtain said $\Delta G_f$; and 3. either a. determining a leachate concentration of said glass composition component in said aqueous solution from the formula:

$$\log_{10}(N\ C_i(g/L)) = a_i + b_i \Delta Gf$$

wherein N $C_i$ is the normalized release of said glass composition component in grams of said glass composition per liter of said aqueous solution, and is equal to $C_i/F_i$, where $C_i$ is the leachate concentration of said glass composition component in said aqueous solution in grams per liter and $F_i$ is the weight fraction (element wt %) of said glass composition component in said glass composition in grams of said glass composition component per grams of glass, and wherein $a_i$ and $b_i$ are constant values for said glass composition component, or b. comparing said $\Delta G_f$ to known values for glasses determined to be stable under the leachate conditions, and 4. comparing at least one of said determined leachate concentrations to an allowable standard for said component of said glass composition, comprising determining the difference between said allowable standard for said component in said glass composition and said determined leachate concentration, and B. determining whether said difference between said allowable standard for said component in said glass composition and said predicted leachate concentration exceeds a preset value; and 1. when said preset value is exceeded, introducing said glass-forming feedstock materials to said melter, or 2. when said preset value is not exceeded, adjusting said composition of said glass-forming feedstock materials and redetermining said difference until said preset value is exceeded.

2. The process according to claim 1, wherein said determining said preliminary glass dissolution estimator, $\Delta G_p$, comprises:

A. selecting glass hydration reaction reactant species;

B. selecting glass hydration reaction product species;

C. determining partial molar hydration free energy changes, $\Delta G_i$, for each chemically and electrically balanced hydration reaction of said glass hydration reaction reactant species in said aqueous solution to form said glass hydration reaction product species;

D. weighting said partial molar hydration free energy changes by the mole fraction of the corresponding glass hydration reaction reactant species; and E. summing said weighted partial molar hydration free energies to obtain said $\Delta G_p$.

3. The process according to claim 2, wherein said selecting said glass hydration reaction product species comprises selecting products of hydration reactions of said glass hydration reaction reactant species which are indicated by Pourbaix solution pH—oxidation potential diagrams to be thermodynamically stable at the pH and Eh of said aqueous solution.

4. The process according to claim 2, wherein said partial molar hydration free energy changes are those associated with (a) release of cationic species to said aqueous solution by ion exchange with hydrogen ions in said aqueous solution, (b) dissolution of a matrix of polymerized $(SiO_4)^{-4}$, $(BO_4)^{-5}$, $(BO_3)^{-3}$, or a combination thereof, (c) surface layer formation of co-precipitated gels, (d) oxidative dissolution of reduced glass reactant species, or (e) a combination thereof.

5. The process according to claim 4, wherein said partial molar hydration free energy changes are selected from the table below:

| Hydration Reactions | $\Delta G_i$ (kcal/mole) | pH Range |
|---|---|---|
| $Al_2O_3 + H_2O \leftrightarrow 2AlO_2^- (aq) + 2H^+ (aq)$ | +37.68 | 7–14 |
| $AmO_2 + 3H_2O \leftrightarrow Am(OH)_5^- (aq) + H^+ (aq)$ | +23.92 | 7–14 |
| $As_2O_3 + 3H_2O + O_2 \leftrightarrow 2HAsO_4^{-2} (aq) + 4H^+ (aq)$ | −33.65 | 7–11 |
| $B_2O_3 + 3H_2O \leftrightarrow 2H_3BO_3 (aq)$ | −10.43 | 7–10 |
| $\{BaO + SiO_2\} + 2H_2O \leftrightarrow Ba(OH)_2 + H_2SiO_3 (aq)$ | −19.13 | 7–14 |
| $\{CaO + SiO_2\} + 2H_2O \leftrightarrow Ca(OH)_2 + H_2SiO_3 (aq)$ | −9.74 | 7–14 |
| $\{CdO + SiO_2\} + 2H_2O \leftrightarrow Cd(OH)_2 + H_2SiO_3(aq)$ | +2.31 | 7–14 |
| $Ce_2O_3 + 3H_2O \leftrightarrow 2Ce(OH)_3$ | −44.99 | 7–14 |
| $\{CoO + SiO_2\} + 5/2 H_2O + 1/4 O_2 \leftrightarrow Co(OH)_3 + H_2SiO_3 (aq)$ | −2.33 | 7–14 |
| $Cr_2O_3 + 3H_2O \leftrightarrow 2Cr(OH)_3$ | +11.95 | 7–14 |
| $\{Cs_2O + SiO_2\} + 2H_2O \leftrightarrow 2Cs^+ (aq) + 2OH^- (aq) + H_2SiO_3 (aq)$ | −76.33 | 7–14 |
| $\{Cu_2O + SiO_2\} + 1/2 O_2 + 3H_2O \leftrightarrow 2Cu(OH)_2 + H_2SiO_3 (aq)$ | −18.85 | 7–14 |
| $\{CuO + SiO_2\} + 2H_2O \leftrightarrow Cu(OH)_2 + H_2SiO_3 (aq)$ | +5.59 | 7–14 |
| $\{FeO + SiO_2\} 1/4 O_2 + 5/2 H_2O \leftrightarrow Fe(OH)_3 + H_2SiO_3 (aq)$ | −17.28 | 7–14 |
| $Fe_2O_3 + 3H_2O \leftrightarrow 2Fe(OH)_3$ | +14.56 | 7–14 |
| $\{K_2O + SiO_2\} + 2H_2O \leftrightarrow 2K^+ (aq) + 2OH^- (aq) + H_2SiO_3 (aq)$ | −72.36 | 7–14 |
| $La_2O_3 + 3H_2O \leftrightarrow 2La(OH)_3$ | −48.59 | 7–14 |
| $\{Li_2O + SiO_2\} + 2H_2O \leftrightarrow 2Li^+ (aq) + 2OH^- (aq) + H_2SiO_3 (aq)$ | −19.99 | 7–14 |
| $\{MgO + SiO_2\} + 2H_2O \leftrightarrow Mg(OH)_2 + H_2SiO_3 (aq)$ | −2.52 | 7–14 |
| $\{MnO + SiO_2\} + 1/2 O_2 + H_2O \leftrightarrow Mn(OH)_2 + H_2SiO_3 (aq)$ | −20.39 | 7–14 |
| $MoO_3 + H_2O \leftrightarrow 2H^+ (aq) + MoO_4^{-2} (aq)$ | +16.47 | 7–14 |
| $\{Na_2O + SiO_2\} + 2H_2O \leftrightarrow 2Na + (aq) + 2OH^- (aq) + H_2SiO_3 (aq)$ | −49.04 | 7–14 |
| $Nd_2O_3 + 3H_2O \leftrightarrow 2Nd(OH)_3$ | −37.79 | 7–14 |
| $\{NiO + SiO_2\} + 2H_2O \leftrightarrow Ni(OH)_2 + H_2SiO_3 (aq)$ | +4.42 | 7–14 |

-continued

| Hydration Reactions | $\Delta G_i$ (kcal/mole) | pH Range |
|---|---|---|
| $P_2O_5 + 3H_2O \leftrightarrow 2HPO_4^{-2}$ (aq) $+ 4H^+$ (aq) | −26.55 | 7–12 |
| $\{PbO + SiO_2\} + 2H_2O \leftrightarrow NPbO_2^-$ (aq) $+ H_2SiO_3$ (aq) $+ H^+$ (aq) | +25.10 | 7–14 |
| $PuO_2 + 3H_2O \leftrightarrow Pu(OH)_5^-$ (aq) $+ H^+$ (aq) | +30.75 | 7–14 |
| $\{Rb_2O + SiO_2\} + 2H_2O \leftrightarrow 2Rb^+$ (aq) $+ 2OH^-$ (aq) $+ H_2SiO_3$ (aq) | −82.18 | 7–14 |
| $RuO_2 + \frac{1}{2}O_2 + H_2O \leftrightarrow RuO_4^-$ (aq) $+ 2H^+$ (aq) | +57.30 | 7–10 |
| $Sb_2O_3 + O_2 + H_2O \leftrightarrow 2SbO_3^-$ (aq) $+ 2H^+$ (aq) | −37.56 | 7–14 |
| $SeO_2 + \frac{1}{2}O_2 + H_2O \leftrightarrow SeO_4^{-2}$ (aq) $+ 2H^+$ (aq) | −7.8 | 7–14 |
| $SiO_2 + H_2O \leftrightarrow H_2SiO_3$ (aq) | +4.05 | 7–10 |
| $SnO_2 + 2H_2O \leftrightarrow Sn(OH)_4$ | +10.16 | 7–12 |
| $\{SrO + SiO_2\} + 2H_2O \leftrightarrow Sr(OH)_2 + H_2SiO_3$ (aq) | −15.67 | 7–14 |
| $TcO_2 + \frac{1}{2}O_2 + H_2O \leftrightarrow TcO_4^-$ (aq) $+ 2H^+$ (aq) | −2.04 | 7–14 |
| $TeO_2 + \frac{1}{2}O_2 + H_2O \leftrightarrow TeO_4^{-2}$ (aq) $+ 2H^+$ (aq) | +12.02 | 7–14 |
| $ThO_2 + H_2O \leftrightarrow Th(OH)_4$ | +19.23 | 7–14 |
| $TiO_2 + H_2O \leftrightarrow TiO(OH)_2$ | +16.27 | 7–14 |
| $U_3O_8 + \frac{1}{2}O_2 + 6H_2O \leftrightarrow 3(UO_3 \cdot 2H_2O)$ | −23.77 | 7–14 |
| $Y_2O_3 + 3H_2O \leftrightarrow 2Y(OH)_3$ | −12.91 | 7–14 |
| $\{ZnO + SiO_2\} + 2H_2O \leftrightarrow Zn(OH)_2 + H_2SiO_3$ (aq) | +4.97 | 7–14 |
| $ZrO_2 + H_2O \leftrightarrow HZrO_3^-$ (aq) $+ H^+$ (aq) | +17.49 | 7–14 |

6. The process according to claim 2, wherein said selecting said glass hydration reaction reactant species comprises selecting one or more of glass reactant species, aqueous reactant species, and optionally gaseous reactant species.

7. The process according to claim 6, wherein said selecting said aqueous reactant species comprises selecting $H^+$ as said aqueous reactant in solutions having a pH<7, and selecting OH or $H_2O$ as said aqueous reactant in solutions having a pH>7.

8. The process according to claim 7, wherein said solution has a pH>7 and said selecting said aqueous reactant comprises selecting $H_2O$.

9. The process according to claim 6, wherein said selecting said gaseous reactant species comprises determining whether said aqueous solution contains reduced species capable of reacting with molecular oxygen in said aqueous solution, and selecting said molecular oxygen as said gaseous reactant species when said reduced species are present.

10. The process according to claim 6, wherein said selecting said gaseous reactant species comprises determining whether said aqueous solution contains reduced species capable of reacting with carbon dioxide in said aqueous solution, and selecting said carbon dioxide as said gaseous reactant species when said reduced species are present.

11. The process according to claim 6, wherein said selecting said glass reactant species comprises selecting oxide species of cations in a glass structure of said glass composition that are either network formers, network modifiers, or intermediate role cations.

12. The process according to claim 11, wherein said network formers comprise oxide species of cations having high atomic field strengths.

13. The process according to claim 11, wherein said network modifiers comprise oxide species of cations having low atomic field strengths which are highly anionically associated with $(SiO_4)^{-4}$ tetrahedra.

14. The process according to claim 11, wherein said intermediate role cations comprise oxide species of cations which are not highly anionically associated with $(SiO_4)^{-4}$ tetrahedra.

15. The process according to claim 1, wherein said determining said free energy associated with the dissociation of silicic acid or boric acid or both at said determined pH, $\Delta G_a^{WA}$, comprises calculating $\Delta G_a^{WA}$ from the following formula:

$$\frac{\Delta G_a^{WA}}{-1.364} = \log_{10}\left(1 + \frac{10^{-10}}{10^{-pH_{det}}} + \frac{10^{-21.994}}{10^{-2pH_{det}}}\right) + \log_{10}\left(1 + \frac{10^{-9.18}}{10^{-pH_{det}}} + \frac{10^{-21.89}}{10^{-2pH_{det}}} + \frac{10^{-35.69}}{10^{-3pH_{det}}}\right)$$

wherein $pH_{det}$ is said determined pH of said aqueous solution of said glass composition.

16. The process according to claim 1, wherein said determining said free energy change associated with accelerated matrix dissolution at said determined pH, $\Delta G_a^{SB}$, comprises:

A. determining accelerated matrix dissolution hydration reactions occurring at said determined pH;

B. determining an accelerated matrix dissolution partial molar hydration free energy change associated with each accelerated matrix dissolution hydration reaction occurring at said determined pH;

C. weighting said accelerated matrix dissolution partial molar hydration free energy changes by the mole fraction of the corresponding accelerated matrix dissolution hydration reactant species; and summing said weighted accelerated matrix dissolution partial molar hydration free energy changes to obtain said $\Delta G_a^{SB}$.

17. The process according to claim 16, wherein said determined pH falls into one or more of the following pH ranges, wherein said accelerated matrix dissolution partial molar hydration reaction comprises one or more of the following reactions occurring in said pH ranges, and wherein said accelerated matrix dissolution partial molar hydration reaction free energy change for said reaction is shown below:

| | $\Delta G_i$ (kcal/mole) | pH Range |
|---|---|---|
| $SiO_2 + OH^-$ (aq) $\leftrightarrow HSiO_3^-$ (aq) | −1.5 | 11–12 |
| $SiO_2 + 2OH^-$ (aq) $\leftrightarrow SiO_3^{-2}$ (aq) $+ H_2O$ | −2.82 | 12–14 |
| $B_2O_3 + H_2O + 2OH^-$ (aq) $\leftrightarrow 2H_2BO_3^-$ (aq) | −23.37 | 11–12.5 |
| $B_2O_3 + 4OH^-$ (aq) $\leftrightarrow 2HBO_3^{-2}$ (aq) $+ H_2O$ | −24.29 | 12.5–13.5 |
| $B_2O_3 + 6OH^-$ (aq) $\leftrightarrow 2BO_3^{-3}$ (aq) $+ 3H_2O$ | −24.85 | >14.5 |
| $RuO_2 + \frac{1}{2}O_2 + H_2O \leftrightarrow RuO_4^{-2}$ (aq) $+ 2H^+$ (aq) | +43.80 | 11–14 |
| $TeO_2 + 2H_2O \leftrightarrow HTeO_4^-$ (aq) $+ 3H^+$ (aq) | +54.54 | 11–14 |

-continued

| | $\Delta G_i$ (kcal/mole) | pH Range |
|---|---|---|
| $P_2O_5 + H_2O + 2OH^- \text{ (aq)} \rightleftharpoons 2PO_4^{-3} \text{ (aq)} + 4H^+$ | −31.07 | 12–14 |
| $SnO_2 + H_2O \rightleftharpoons SnO_3^{-2} \text{ (aq)} + 2H^+ \text{ (aq)}$ | +43.55 | 12–14 |

18. The process according to claim 1, wherein at least one of said components of said glass comprises a radioactive isotope or element, or a hazardous material, or a mixture thereof.

19. The process according to claim 18, wherein said hazardous material contains a metal selected from the group consisting of Ba, As, Cd, Cr, Pb, Se, Ag, Zn, Ni, U, Th, Cs, Am, Ce, Nd, La, Co, Tc, Te, Pu, and mixtures thereof.

20. The process according to claim 18, wherein said aqueous solution comprises groundwater and is present in a geological nuclear or hazardous waste repository or vault.

21. The process according to claim 1, wherein said component of said glass composition is one or more components selected from the group consisting of boron, lithium, sodium, or silicon.

22. The process according to claim 21, wherein said component in said glass composition is boron, said $a_i$ is around −1.535, and said $b_i$ is around −0.104.

23. The process according to claim 21, wherein said component in said glass composition is lithium, said $a_i$ is around −1.249, and said $b_i$ is around −0.0847.

24. The process according to claim 21, wherein said component of said glass composition is sodium, said $a_i$ is around −1.448, and said $b_i$ is around −0.0981.

25. The process according to claim 21, wherein said component of said glass composition is silicon, said $a_i$ is around −1.424, and said $b_i$ is around −0.762.

26. The process according to claim 1, further comprising:
   E. determining whether said glass composition will be homogeneous or phase separated, comprising:
      1. determining a frit component function, x, which is the sum of the amounts of all sources of alkali oxide species, the amount of $B_2O_3$, and the amount of $SiO_2$, in percent by weight;
      2. determining a sludge component function, y, which is the sum of the amounts of $Al_2O_3$, $Fe_2O_3$, FeO calculated as $Fe_2O_3$, $Nd_2O_3$, $Ce_2O_3$, $La_2O_3$, $Y_2O_3$, CaO, and $MoO_3$, in percent by weight;
      3. determining whether x and y meet the phase separation inequality: −1.6035 x−5.6478 y+210.9203<0; and
      4. when said inequality is met, introducing said glass-forming feedstock materials to said melter, or
      5. when said inequality is not met, adjusting said composition of said glassforming feedstock materials, redetermining x and y, and redetermining whether said inequality is met, until said inequality is met, and then introducing said glass-forming feedstock materials to said melter.

27. The process according to claim 1, wherein at least one of said glass-forming feedstock materials comprises radioactive waste material.

28. The process according to claim 27, wherein said glass composition is suitable for storage in a geological nuclear or hazardous waste repository or vault.

29. A process for preparing a glass composition at least partially soluble in a body fluid solution, comprising:
   A. determining the composition of glass-forming feedstock materials to be fed to a melter;
   B. determining a final glass dissolution free energy change, $\Delta G_f$, comprising:
      1. determining a preliminary glass dissolution estimator, $\Delta G_p$;
      2. determining an accelerated glass dissolution function, $\Delta G_a$ comprising:
         a. determining the pH of said aqueous solution of said glass composition;
         b. determining the free energy change associated with the dissociation of silicic acid or boric acid or both at said predicted pH, $\Delta G_a^{WA}$;
         c. determining the free energy change associated with accelerated matrix dissolution at said predicted pH, $\Delta G_a^{SB}$; and
         d. summing said $\Delta G_a^{WA}$ and said $\Delta G_a^{SB}$ to obtain said $\Delta G_a$; and
      3. summing said $\Delta G_p$ and said $\Delta G_a$ to obtain said $\Delta G_f$; and either:
   C. controlling said glass composition based upon a leachate concentration of said glass composition component in said body fluid solution, comprising:
      1. determining a leachate concentration of said glass composition component in said body fluid solution from the formula:

$$\log_{10}(N\ C_i(g/L)) = a_i + b_i \Delta G_f$$

wherein N $C_i$ is the normalized release of said glass composition component in grams of said glass composition per liter of said body fluid solution, and is equal to $C_i/F_i$, where $C_i$ is the leachate concentration of said glass composition component in said body fluid solution in grams per liter and $F_i$ is the fraction of said glass composition component in said glass composition in grams of said glass composition component per grams of glass, and wherein $a_i$ and $b_i$ are constant values for said glass composition component; and
      2. comparing at least one of said determined leachate concentrations to a minimum desired concentration for said component of said glass composition in said body fluid solution; and
         a. when said predicted leachate concentration of said component is higher than said minimum desired concentration, introducing said glass-forming feedstock materials to said melter, or
         b. when said predicted leachate concentration of said component is lower than said minimum desired amount, adjusting said composition of said glass-forming feedstock materials and redetermining said leachate concentration, until said predicted leachate concentration is higher than said minimum desired amount; or
   D. controlling said glass composition based upon said $\Delta G_f$, comprising comparing said $\Delta G_f$ to known values for glasses determined to have acceptable solubilities in a body fluid solution.

30. The process according to claim 29, wherein said body fluid solution is a physiological saline solution.

31. The process according to claim 29, wherein said body fluid solution is in animal lung tissue.

32. The process according to claim 31, wherein said animal lung tissue is a mammalian lung tissue.

33. The process according to claim 32, wherein said mammalian lung tissue is human lung tissue.

34. The process according to claim 29, wherein said determining said preliminary glass dissolution estimator, $\Delta G_p$, comprises:

A. selecting glass hydration reaction reactant species;

B. selecting glass hydration reaction product species;

C. determining partial molar hydration free energy changes, $\Delta G_i$, for each chemically and electrically balanced hydration reaction of said glass hydration reaction reactant species in said body fluid solution to form said glass hydration reaction product species;

D. weighting said partial molar hydration free energy changes by the mole fraction of the corresponding glass hydration reaction reactant species; and E. summing said weighted partial molar hydration free energies, $\Delta G_i$, to obtain said $\Delta G_p$.

35. The process according to claim 29, further comprising:

E. determining whether said glass composition will be homogeneous or phase separated, comprising:

1. determining a frit component function, x, which is the sum of the amounts of all sources of alkali species, the amount of $B_2O_3$, and the amount Of $SiO_2$, in percent by weight;

2. determining a sludge component function, y, which is the sum of the amounts of $Al_2O_3$, $Fe_2O_3$, FeO calculated as $Fe_2O_3$, $Nd_2O_3$, $Ce_2O_3$, $La_2O_3$, $Y_2O_3$, CaO, and $MoO_3$, in percent by weight;

3. determining whether x and y meet the phase separation inequality: $-1.6035 x - 5.6478 y + 210.9203 < 0$; and 4. when said inequality is not met, introducing said glass-forming feedstock materials to said melter, or 5. when said inequality is met, adjusting said composition of said glass-forming feedstock materials, redetermining x and y, and redetermining whether said inequality is not met, until said inequality is not met, and then introducing said glass-forming feedstock materials to said melter.

* * * * *